US007427598B2

(12) United States Patent
Spong et al.

(10) Patent No.: US 7,427,598 B2
(45) Date of Patent: *Sep. 23, 2008

(54) POST-NATAL ADMINISTRATION OF ACTIVITY-DEPENDENT NEUROTROPHIC FACTOR-DERIVED POLYPEPTIDES FOR ENHANCING LEARNING AND MEMORY

(75) Inventors: Catherine Y. Spong, Arlington, VA (US); Douglas Brenneman, Lansdale, PA (US); Illana Gozes, Ramat Hasharon (IL)

(73) Assignees: The United States of Americas as represented by the Secretary of the Department of Health and Human Services, Washington, DC (US); Ramot at Tel-Aviv University, Ltd., Tel Aviv (IL)

( * ) Notice: Subject to any disclaimer, the term of this patent is extended or adjusted under 35 U.S.C. 154(b) by 92 days.

This patent is subject to a terminal disclaimer.

(21) Appl. No.: 10/296,849

(22) PCT Filed: May 31, 2001

(86) PCT No.: PCT/US01/17758

§ 371 (c)(1),
(2), (4) Date: Nov. 27, 2002

(87) PCT Pub. No.: WO01/92333

PCT Pub. Date: Dec. 6, 2001

(65) Prior Publication Data

US 2004/0048801 A1    Mar. 11, 2004

(51) Int. Cl.
*A61K 38/08* (2006.01)
*A61K 38/10* (2006.01)
(52) U.S. Cl. .......................................... 514/16; 514/15
(58) Field of Classification Search ........................ None
See application file for complete search history.

(56) References Cited

U.S. PATENT DOCUMENTS

| 4,587,046 | A | * | 5/1986 | Goodman et al. ........... 530/330 |
| 5,767,240 | A | | 6/1998 | Brenneman et al. |
| 6,174,862 | B1 | * | 1/2001 | Brenneman ................ 514/15 |
| 6,613,740 | B1 | | 9/2003 | Gozes et al. |
| 6,933,277 | B2 | | 8/2005 | Brenneman et al. |
| 2004/0053313 | A1 | | 3/2004 | Gozes et al. |

FOREIGN PATENT DOCUMENTS

| EP | 1 206 489 B1 | 5/2004 |
| WO | WO 92/18140 A1 | 10/1992 |
| WO | WO 96/11948 A1 | 4/1996 |
| WO | WO 98/35042 | * 8/1998 |
| WO | WO 98/35042 A1 | 8/1998 |
| WO | WO 00/27875 A2 | 5/2000 |
| WO | WO 00/53217 A2 | 9/2000 |
| WO | WO 01/12654 A2 | 2/2001 |

OTHER PUBLICATIONS

Bassan et al. 1999. Journal of Neurochemistry 72:1283-1293.*
Voet 1995. Biochemistry, Second Edition, p. 67.*
Spong 1999. Society for Neuroscience Abstracts 25(1):405-9.*
Guptasarma 1992. FEBS Letters 310:205-210.*
Bassan, M. et al. "VIP-Induced Mechanism of Neuroprotection: The Complete Sequence of a Femtomolar-Acting Activity-Dependent Neuroprotective Protein." *Regulatory Peptides*, vol. 71, No. 2, (Aug. 15, 1997).
Bassan, M. et al. "Complete Sequence of a Novel Protein Containing a Femtomolar-Activity-Dependent Neuroprotective Peptide." *Journal of Neurochemistry*, vol. 72, pp. 1283-1293 (1999).
Beni-Adani, L. et al. "Activity-Dependent Neurotrophic Protein is Neuroprotective in a Mouse Model of Closed Head Injury." Society for Neuroscience, 28th Annual Meeting, Los Angeles, CA, Nov. 7-12, 1998. *Abstracts*, vol. 23, Part 1, p. 1043 (1998).
Brenneman, D.C. and Gozes, I. "A Femtomolar-Acting Neuroprotective Peptide." *Journal of Clinical Investigation*, vol. 97, pp. 2299-2307 (1996).
Brenneman et al. "Neuronal Cell Killing by the Envelope Protein of HIV and Its Prevention by Vasoactive Intestinal Peptide." *Nature* 335:636 (1988).
Brenneman et al. "*N*-Methyl-D-Aspartate Receptors Influence Neuronal Survival in Developing Spinal Cord Cultures" *Dev. Brain Res.* 51:63 (1990).
Brenneman, D.E. et al. "Identification of a Nine Amino Acid Core Peptide from Activity Dependent Neurotrophic Factor I." Society for Neuroscience, 27th Annual Meeting, New Orleans, LA, Oct. 25-30, 1997. *Abstracts*, vol. 23, Part 2, p. 2250 (1997).
Brenneman, D.E. et al. "Activity-Dependent Neurotrophic Factor: Structure-Activity Relationships of Femtomolar-Acting Peptides." *Journal of Pharmacology and Experimental Therapeutics*, vol. 285, pp. 619-627 (1998).
Davidson, A. et al. "Protection Against Developmental Retardation and Learning Impairments in Apolipoprotein E-Deficient Mice by Activity-Dependent Femtomolar-Acting Peptides." Society for Neuroscience, 27th Annual Meeting, New Orleans, LA, Oct. 25-30, 1997. *Abstracts*, vol. 23, Part 2, p. 2250 (1997).
Dibbern, D.A., Jr. et al. "Inhibition of Murine Embryonic Growth by Human Immunodeficiency Virus Envelope Protein and Its Prevention by Vasoactive Intestinal Peptide and Activity-Dependent Neurotrophic Factor." *Journal of Clinical Investigation*, vol. 99, pp. 28377-2841 (1997).
GenBank Accession No. AB018327 from the DNA Data Bank of Japan (DDBJ) (released Nov. 17, 1998).
Giladi, E. "Protection Against Developmental and Learning Impairments in Apolipoprotein E-Deficient Mice by Activity-Dependent Femtomolar-Acting Peptides." *Neuroscience Letters*, Supplement 48 S1-S60, p. S19 (1997).

(Continued)

*Primary Examiner*—Daniel E. Kolker
(74) *Attorney, Agent, or Firm*—Townsend and Townsend and Crew LLP

(57) ABSTRACT

The present invention provides methods for improving performance (e.g. learning and/or memory) using (ADNF) polypeptides, by treating the subject prenatally or postnatally with an Activity Dependent Neurotrophic Factor (ADNF) polypeptide in an amount sufficient to improve postnatal learning and/or memory of the subject.

22 Claims, 19 Drawing Sheets

OTHER PUBLICATIONS

Glazner, G.W. et al. "A 9 Amino Acid Peptide Fragment of Activity-Dependent Neurotrophic Factor (ADNF) Protects Neurons from Oxidative Stress-Induced Death." Society for Neuroscience, 27th Annual Meeting, New Orleans, LA, Oct. 25-30, 1997. *Abstracts*, vol. 23, Part 2, p. 2249 (1997).

Glazner, G.W. et al. "Activity Dependent Neurotrophic Factor: A Potent Regulator of Embryonic Growth." *Anat. Embryol.* 200:65-71 (1999).

Gozes, I. and Brenneman, D.E. "Activity-Dependent Neurotrophic Factor (ADNF)." *Journal of Molecular Neuroscience*, vol. 7, pp. 235-244 (1996).

Gozes, I. et al. "Stearyl-Norleucine-Vasoactive Intestinal Peptide (VIP): A novel VIP Analog for Noninvasive Impotence Treatment." *Endocrinology*, vol. 134, pp. 2125 (1994).

Gozes, I. et al. "Superactive Lipophilic Peptides Discriminate Multiple Vasoactive intestinal Peptide Receptors." *Journal of Pharmacology and Experimental Therapeutics*, vol. 273, pp. 161-167 (1995).

Gozes, I. et al. "Neuroprotective Strategy for Alzheimer Disease: Intranasal Administration of a Fatty Neuropeptide." *Proc. Natl. Acad. Sci. USA*, vol. 93, pp. 427-432 (1996).

Gozes I. et al. "Antiserum to Activity-Dependent Neurotrophic Factor Produces Neuronal Cell Death in CNS Cultures: Immunological and Biological Specificity." *Developmental Brain Research*, vol. 99, pp. 167-175 (1997).

Gozes, I. et al. A Femtomolar-Acting Activity-Dependent Neuroprotective Protein (ADNP). *Neuroscience Letters*, Supplement 48 S1-S60, p. S21 (1997).

Gozes, I. et al. "Protection Against Developmental Retardation in Apolipoprotein E-Deficient Mice by a Fatty neuropeptide: Implications for Early Treatment of Alzheimer's Disease." *Journal of Neurobiology*, vol. 33, pp. 329-342 (1997).

Gozes, I. et al. "The cDNA Structure of a Novel Femtomolar-Acting Neuroprotective Protein: Activity-Dependent-Neurotrophic Factor III (ADNFIII)." Society for Neuroscience, 27th Annual Meeting, New Orleans, LA, Oct. 25-30, 1997. *Abstracts*, vol. 23, Part 2, p. 2250 (1997).

Gozes, et al., "A Novel Signaling Molecule for Neuropeptide Action: Activity-dependent Neuroprotective Protein"; Annals of the New York Academy of Sciences, 897:125-135 (1999).

Gozes, I. et al. "Activity-dependent neurotrophic factor: Intranasal administration of femtomolar-acting peptides improve performance in a water maze" *Journal of Pharmacology and Experimental Therapeutics*, vol. 293, pp. 1091-1098 (2000).

Gressens, P. et al. "Growth Factor Function of Vasoactive Intestinal Peptide in Whole Cultured Mouse Embryos." *Nature* 362:155-58 (1993).

Hannigan, J.H. and Berman, R.F. "Amelioration of Fetal Alcohol-Related Neurodevelopmental Disorders in Rats: Exploring Pharmacological and Environmental Treatments." *Neurotoxicol. & Teratol.* 22(1):103-111 (2000).

Hill, J.M. et al. "Learning Impairment in Adult Mice Produced by Early Embryonic Administration of Antiseum to Activity-Dependent Neurotrophic Factor (ADNF)." Society for Neuroscience, 27th Annual Meeting, New Orleans, LA, Oct. 25-30, 1997. *Abstracts*, vol. 23, Part 2, p. 2250 (1997).

Lilling, G. et al. "Inhibition of Human Neuroblastoma Growth by a Specific VIP Antagonist." *Journal of Molecular Neuroscience*, vol. 5, pp. 231-239 (1995).

Mahato et al. "Development of Targeted Delivery Systems for Nucleic Acid Drugs." *J. of Drug Targeting* 4(6):337-357 (1997) [Abstract].

McKune, S.K. et al. "Localization of mRNA for Activity-Dependent Neurotrophic Factor III (ADNF III) in mouse Embryo and Adult CNS." Society for Neuroscience, 27th Annual Meeting, New Orleans, LA, Oct. 25-30, 1997. *Abstracts*, vol. 23, Part 2, p. 2249 (1997).

Nagase, et al., "Prediction of the Coding Sequences of Unidentified Human Genes. XI. The Complete Sequences of 100 New cDNA Clones from Brain Which Code for Large Proteins in vitro"; DNA Research 5:5:277-286 (1998).

Nelbock, P. et al. A cDNA for a Protein that Interacts with the Human Immunodeficiency Virus Tat Transactivator. *Science*, vol. 248, pp. 1650-1653 (1990).

Oberdoester, J. et al. "The Effects of Ethanol on Neuronal Cell Death: Implication for the Fetal Alcohol Syndrome." *FASEB Journal* 12(4):A134 (Mar. 17, 1998).

Pelsman, A. et al. "In Vitro Degeneration of Down Syndrome neurons is Prevented by Activity-Dependent Neurotrophic Factor-Derived Peptides." Society for Neuroscience, 28TH Annual Meeting, Los Angeles, CA, Nov. 7-12, 1998. *Abstracts*, vol. 24, p. 1044 (1998).

Skolnick, J. and Fetrow, J.S. "From Genes to Protein Structure and Function: Novel Applications of Computational Approaches in the Genomic Era." *Trends in Biotech.* 18(1):34-39 (2000).

Smith, A.E. "Viral Vectors in Gene Therapy." *Ann. Rev.Microbiol.* 49:807-838 (1995) [Abstract].

Spinney, L. "New Peptides Prevent Brain Damage." *Molecular Medicine Today* 5(7):282 (Jul. 1999).

Spong et al. "Prevention of Fetal Alcohol Syndrome by Novel Peptides." *FASEB Journal* 13(5):A881 (Mar. 15, 1991).

Spong et al. "Prevention of Fetal Demise and Growth Restriction in a Mouse Model of Fetal Alcohol Syndrome" *The Journal of Pharmacology and Experimental Therapeutics* 297:774-779 (2001).

Voet et al. *Biochemistry, 2nd Ed.*, p. 67, 1995.

Wilkemeyer et al. "Differential effects of ethanol antagonism and neuroprotection in peptide fragment NAPVSIPQ prevention of ethanol-induced developmental toxicity" *PNAS* 100:8543-8548 (2003).

Spong et al. "Prevention of Fetal Alcohol Syndrome by Novel Peptides." *FASEB Journal* 13(5):A881 (Mar. 15, 1999).

* cited by examiner

○ Control

● Control + ADNF-9

□ AF-64A

■ AF-64A + ADNF-9

$*p<0.001$ in comparison to all experimental groups

*p<0.001 NAP-treated are significantly different than the respective vehicle-treated control or AF64-animals

**p<0.001 NAP-treated are significantly different than the respective vehicle-treated AF64-animals

* $p < 0.001$ in comparison to all experimental groups

* $p<0.022$ the AF64A+ADNF-9 group compared to AF64A+NAP

** $p<0.013$ AF64A as compared to control AF64A+ADNF-9 as compared to control

POST-NATAL ADMINISTRATION OF ACTIVITY-DEPENDENT NEUROTROPHIC FACTOR-DERIVED POLYPEPTIDES FOR ENHANCING LEARNING AND MEMORY

THE ADNF I polypeptides have an active core site comprising the following amino acid sequence: Ser-Ala-Leu-Leu-Arg-Ser-Ile-Pro-Ala ("SALLRSIPA" or in short referred to as "SAL" or "ADNF-9"; SEQ ID NO:1). The ADNF III polypeptides also have an active core site comprising a few amino acid residues, namely, the following amino acid sequence: Asn-Ala-Pro-Val-Ser-Ile-Pro-Gln ("NAPVSIPQ" or in short referred as "NAP"; SEQ ID NO:2). These ADNF polypeptides have previously been shown, each on their own, to have remarkable potency and activity in animal models related to neurodegeneration.

In one embodiment of the present invention, it is discovered that upon post-natal administration, the ADNF polypeptides also improve performance, such as learning and memory, in animal models that are afflicted with, e.g., neuropathology, Alzheimer's disease, Down's syndrome, age, or mental retardation (e.g., fragile X syndrome), as well as normal animals. The polypeptides of the invention can also be used to improve short term and reference memory.

As such, applications for the ADNF polypeptides of the present invention include improving the performance of subjects with, e.g., neuropathology; sensory-motor problems; improving the performance of subjects impaired in cognitive tasks; improving the performance of subjects with memory deficiencies; improving the performance of normal subjects; and the like. Accordingly, embodiments of the invention in suitable formulations, can be employed for decreasing the amount of time needed to learn a cognitive, motor or perceptual task. Alternatively, invention compounds, in suitable formulations, can be employed for increasing the time for which cognitive, motor or perceptual tasks are retained. As another alternative, embodiments of the invention in suitable formulations, can be employed for decreasing the quantity and/or severity of errors made in recalling a cognitive, motor or perceptual task. Such treatment may prove especially advantageous in individuals who have suffered injury to the nervous system, or who have endured disease of the nervous system. ADNF polypeptides are administered to the affected individual, and thereafter, the individual is presented with a cognitive, motor or perceptual task. Moreover, ADNF polypeptides can be administered to normal subjects to improve their performance (e.g., learning and memory). ADNF polypeptides can be particularly useful for an aged population in which capacity for memory (e.g., short term) has generally declined.

In another embodiment, the present invention is based, in part, on the discovery that when animals in utero are treated with Activity Dependent Neurotrophic Factor (ADNF) polypeptides, the ADNF polypeptides improved the animals postnatal learning and memory, in particular, spatial learning. Surprisingly, this long term effect of ADNF polypeptides is observed even when a single dose of ADNF polypeptides is prenatally administered in the beginning of pregnancy. Quite surprisingly, this enhanced learning and memory effect of ADNF polypeptides is seen even in animals with normal mental capacity (e.g., normal mice without any mental impairment). Hence, ADNF polypeptides can push normal animals beyond their natural capacity of learning and memory and can improve their cognitive skills.

As described above, these ADNF polypeptides have previously been shown to have remarkable potency and activity in animal models, particularly in those related to neurodegeneration. However, the effects of ADNF polypeptides were observed when they were postnatally administered to the animals. It has now been discovered for the first time that the prenatal treatment with ADNF polypeptides can enhance the animals' postnatal learning and memory, both for normal animals as well as for mentally impaired animals.

The present discovery has significant applications in human subjects in improving their learning, memory, and associated mental processes. Even normal human subjects can benefit from the prenatal treatment with ADNF polypeptides. Moreover, the present discovery has applications in subjects who are mentally compromised. For example, if a fetus is diagnosed as having mental retardation or Down's syndrome, the fetus in utero can be treated with ADNF polypeptides so that its postnatal learning and memory skills can be ameliorated. Even without a specific diagnosis of mental retardation or Down's syndrome, ADNF polypeptides can be prophylactically administered to the fetus in certain circumstances. For example, if there is a family history of mental retardation (e.g., fragile X syndrome), ADNF polypeptides can be prophylactically administered to the fetus in utero. In another example, if the mother is older (e.g., 35 years or older) and thus, has a higher risk of having a baby with Down's syndrome or other genetic defects, ADNF polypeptides can be prophylactically administered to the fetus in utero.

Various parameters can be measured to determine if an ADNF polypeptide or a combination of ADNF polypeptides improves performance (e.g., learning and memory) in vivo. For example, the hidden platform test of the Morris water maize can be used described in the materials and methods section below can be used. Generally, mice that are treated with ADNF polypeptides and control mice (that are not treated with ADNF polypeptides) are trained to escape swimming task by learning the position of a hidden platform and climbing on it. The time it takes them to complete this task is defined as the escape latency. This test can be conducted one or more times daily for a number of days. One parameter that is indicate of improved learning and memory is the reduction in latency in escaping swimming task by climbing onto a hidden platform. See, also, methods described in Gozes et al., *Proc. Natl. Acad. Sci. USA* 93:427-432 (1996), incorporated herein by reference. Animals treated with suitable ADNF polypeptides would show improvement in their learning and memory capacities compared to the control that are not treated with ADNF Polypeptides. Embodiments of the invention are not limited by examples of test used to measure performance. Any suitable test methods can be used to measure performance, such as learning and memory.

Other methods known in the art can be used in human subjects to determine if an ADNF polypeptide or a combination of ADNF polypeptides improves performance (e.g., learning and memory) in vivo. For example, these methods include assessment of memory or learning over time by the Randt Memory Test (Randt et al., *Clin. Neuropsychol.* 2:184 (1980), Wechsler Memory Scale (*J. Psych.* 19:87-95 (1945), Forward Digit Span test (Craik, Age Differences in Human Memory, in: *Handbook of the Psychology of Aging*, Birren and Schaie (Eds.), New York, Van Nostrand (1977), Mini-Mental State Exam (Folstein et al., *J. of Psych. Res.* 12:189-192 (1975), or California Verbal Learning Test (CVLT)). See, also, U.S. Pat. No. 6,030,968. In these tests, factors unrelated to effects of ADNF polypeptides (e.g., anxiety, fatigue, anger, depression, confusion, or vigor) are controlled for. See, U.S. Pat. No. 5,063,206. Methods for assessing and controlling for subjective factors is known in the art and determined by such standard clinical tests such as the BECK Depression Scale, Spielberger Trait State Anxiety test, and POMS test (Profile of Mood State).

In one aspect, the present invention provides a method for improving performance (e.g., learning and/or memory), the method comprising administering either postnatally or prenatally to a subject an Activity Dependent Neurotrophic Factor (ADNF) polypeptide in an amount sufficient to improve postnatal performance (e.g., learning and/or memory). Methods of the invention can be applied to any subjects, e.g., subjects who are afflicted with neuropathology, such Alzheimer's disease, Down's syndrome, etc. or normal subjects, either young or old, or subjects in utero. In one embodiment, the ADNF polypeptide is prenatally administered to the subject who has normal mental capacity. In another embodiment, the subject has mental retardation (e.g., fragile x syndrome), a family history of mental retardation, Down's syndrome, or a mother who is at least 35 years of age when pregnant with the subject. Preferably, if the subject has mental retardation, it is not caused by excessive maternal alcohol consumption during pregnancy (i.e., mental retardation is not part of fetal alcohol syndrome).

In one embodiment, the ADNF polypeptide is administered prenatally, e.g., to a pregnant mother, e.g., by intraperitoneal administration or oral administration. In another embodiment, the ADNF polypeptide is administered postnatally, e.g. by intraperitoneal administration or oral administration. In one embodiment, the ADNF polypeptide is administered at the time of neural tube development and/or closure of the neural tube.

In one embodiment, the method comprises administering an ADNF polypeptide, wherein the ADNF polypeptide is an ADNF I polypeptide comprising an active core site having the amino acid sequence of Ser-Ala-Leu-Leu-Arg-Ser-Ile-Pro-Ala (SEQ ID NO:1)). In another embodiment, the method comprises administering a full length ADNF I polypeptide. In yet another embodiment, the method comprises administering an ADNF I polypeptide which consists of the amino acid sequence of Ser-Ala-Leu-Leu-Arg-Ser-Ile-Pro-Ala (SEQ ID NO:1). In yet another embodiment, the method comprises administering an ADNF I polypeptide, wherein the ADNF I polypeptide is selected from the group consisting of: Val-Leu-Gly-Gly-Gly-Ser-Ala-Leu-Leu-Arg-Ser-Ile-Pro-Ala (SEQ ID NO:14); Val-Glu-Glu-Gly-Ile-Val-Leu-Gly-Gly-Gly-Ser-Ala-Leu-Leu-Arg-Ser-Ile-Pro-Ala (SEQ ID NO:15); Leu-Gly-Gly-Gly-Ser-Ala-Leu-Leu-Arg-Ser-Ile-Pro-Ala (SEQ ID NO:16); Gly-Gly-Gly-Ser-Ala-Leu-Leu-Arg-Ser-Ile-Pro-Ala (SEQ ID NO:17); Gly-Gly-Ser-Ala-Leu-Leu-Arg-Ser-Ile-Pro-Ala (SEQ ID NO:18); and Gly-Ser-Ala-Leu-Leu-Arg-Ser-Ile-Pro-Ala (SEQ ID NO:19). In yet another embodiment, the method comprises administering an ADNF I polypeptide having up to about 20 amino acids at at least one of the N-terminus or the C-terminus of the active core site. In certain embodiments, the ADNF I polypeptide has up to 20 amino acids at both the N-terminus and the C-terminus of the ADNF I polypeptide.

In another embodiment, the method comprises administering an ADNF polypeptide, wherein the ADNF polypeptide is an ADNF III polypeptide comprising an active core site having the amino acid sequence of Asn-Ala-Pro-Val-Ser-Ile-Pro-Gln (SEQ ID NO:2). In yet another embodiment, the method comprises administering a full length ADNF III polypeptide. In yet another embodiment, the method comprises administering an ADNF I polypeptide which consists of the amino acid sequence of Asn-Ala-Pro-Val-Ser-Ile-Pro-Gln (SEQ ID NO:2). In yet another embodiment, the method comprises administering an ADNF III polypeptide, wherein the ADNF In polypeptide is selected from the group consisting of: Gly-Gly-Asn-Ala-Pro-Val-Ser-Ile-Pro-Gln (SEQ ID NO:20); Leu-Gly-Gly-Asn-Ala-Pro-Val-Ser-Ile-Pro-Gln-Gln-Ser (SEQ ID NO:21); Leu-Gly-Leu-Gly-Gly-Asn-Ala-Pro-Val-Ser-Ile-Pro-Gln-Gln-Ser (SEQ ID NO:22); and Ser-Val-Arg-Leu-Gly-Leu-Gly-Gly-Asn-Ala-Pro-Val-Ser-Ile-Pro-Gln-Gln-Ser (SEQ ID NO:23). In yet another embodiment, the method comprises administering an ADNF III polypeptide having up to about 20 amino acids at at least one of the N-terminus and the C-terminus of the active core site. In certain embodiments, the ADNF III polypeptide has up to 20 amino acids at both the N-terminus and the C-terminus of the ADNF III polypeptide.

In yet another embodiment, the method comprises administering a mixture of an ADNF I polypeptide and an ADNF III polypeptide. Any one or more of the ADNF I polypeptides described herein can be mixed with any one or more of the ADNF III polypeptides described herein in this and other aspects of the invention.

In another embodiment, the active core site of the ADNF polypeptide comprises at least one D-amino acid. In another embodiment, the active core site of the ADNF polypeptide comprises all D-amino acids.

In yet another embodiment, at least one of the ADNF polypeptide is encoded by a nucleic acid which is administered to the subject.

In yet another embodiment, the ADNF polypeptide improves a short term memory. In yet another embodiment, the ADNF polypeptide improves a reference memory. In yet another embodiment, the ADNF polypeptide is administered intranasally or orally.

These and other aspects of the present invention will become apparent to those skilled in the art from the following detailed description of the invention, the accompanying drawings, and the appended claims.

DEFINITIONS

Figure 1A:
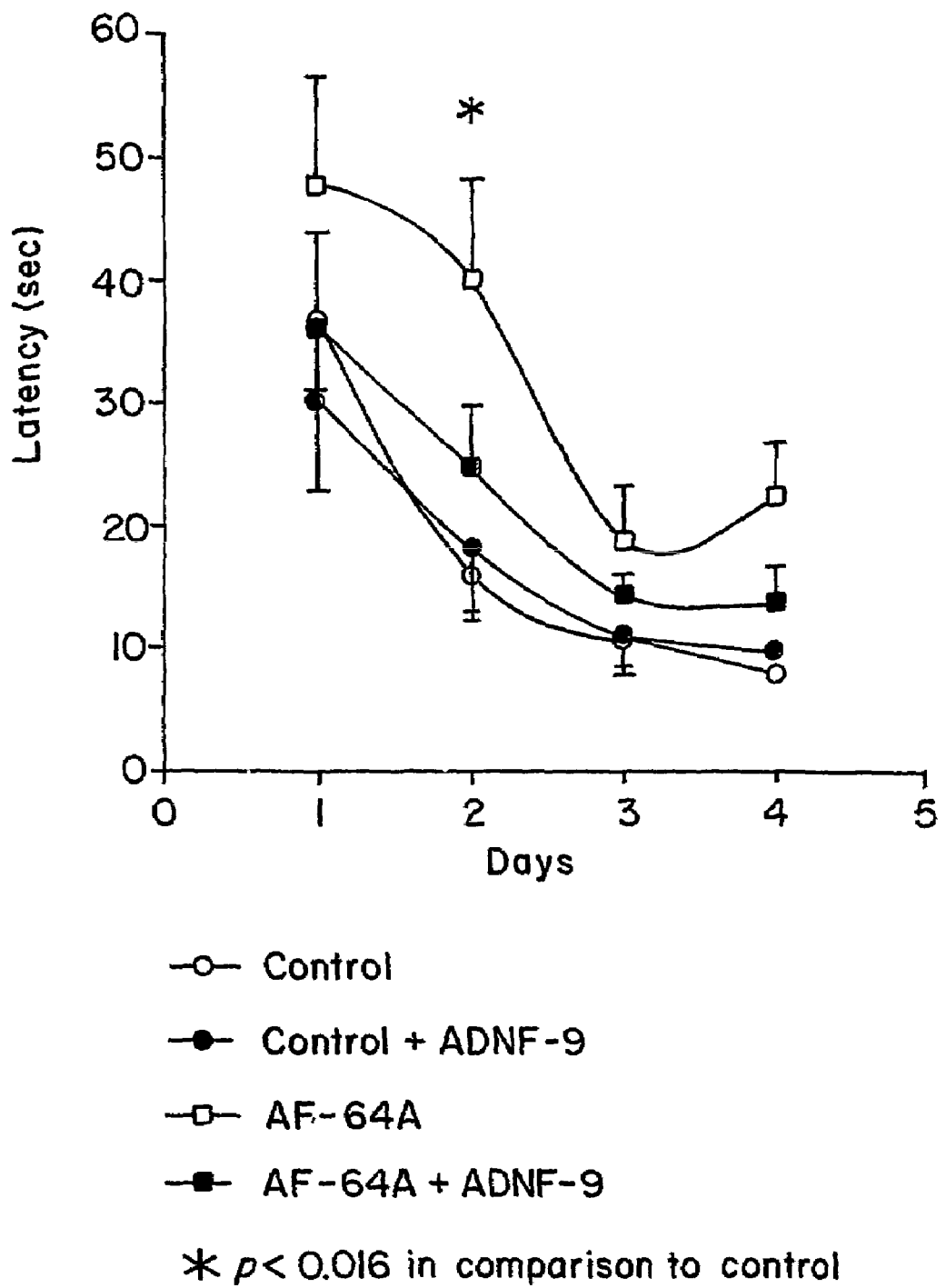
FIG. 1 AF64A-treated rats exhibit an impairment in learning and memory that is ameliorated by intranasal administration of ADNF-9. Two daily water maze tests (A and B, respectively) were performed on adult rats. Groups tested were: 1. control animals treated with vehicle (20 animals, open circles); 2. AF64A-treated animals intranasally administered with vehicle (27 animals, open squares); 3. control animals treated by intranasal administration of ADNF-9 (closed circles, 12 animals); 4. AF64A-treated animals intranasally administered with ADNF-9 (19 animals, closed squares). (A) Latency measured in seconds (mean±standard error of the mean) to reach the hidden platform in its new daily location (indicative of intact reference memory, Gordon et al., *Neurosci. Lett.* 199:14 (1995)) is depicted. Tests were performed over four consecutive days. (B) Latency measured in seconds to reach the hidden platform 0.5 min. after being on it (indicative of intact working memory processes, Gordon et al., *Neurosci. Lett.* 199:1-4 (1995); Gozes et al., *J. Neurobiol.* 33:329-342. (1997a)) tested over four consecutive days. There were no differences between animals treated with vehicle and untreated animals (data not shown). (C) On day 5 of testing, the platform was removed and a spatial probe test was performed. The animals were allowed to swim for 120 sec. and the time spent by the animal at the platform quadrant was recorded.

The phrase "ADNF polypeptide" refers to one or more activity dependent neurotrophic factors (ADNF) that have an active core site comprising the amino acid sequence of SALLRSIPA (referred to as "SAL"; SEQ ID NO:1) or NAPVSIPQ (referred to as "NAP"; SEQ ID NO:2), or conservatively modified variants thereof that have neurotrophic/neuroprotective activity as measured with in vitro cortical neuron culture assays described by, e.g. Hill et al., *Brain Res.* 603, 222-233 (1993); Venner & Gupta, *Nucleic Acid Res.* 18, 5309 (1990); and Peralta et al., *Nucleic Acid Res.* 18, 7162 (1990); Brenneman et al., *Nature* 335, 636 (1988); or Brenneman et al., *Dev. Brain Res.* 51:63 (1990); Forsythe & Westbrook, *J. Physiol. Lond.* 396:515 (1988). An ADNF polypeptide can be an ADNF I polypeptide, an ADNF III polypeptide, their alleles, polymorphic variants, analogs, interspecies homolog, or any subsequences thereof (e.g. SALLRSIPA; SEQ ID NO:1 or NAPVSIPQ; SEQ ID NO:2) that exhibit neuroprotective/neurotrophic action on, e.g., neurons originating in the central nervous system either in vitro or in vivo. An "ADNF polypeptide" can also refer to a mixture of an ADNF I polypeptide and an ADNF III polypeptide.

The term "ADNF I" refers to an activity dependent neurotrophic factor polypeptide having a molecular weight of about 14,000 Daltons with a pI of 8.3±0.25As described above, ADNF I polypeptides have an active site comprising an amino acid sequence of Ser-Ala-Leu-Leu-Arg-Ser-Ile-Pro-Ala (also referred to as "SALLRSIPA" or "SAL" or "ADNF-9"; SEQ ID NO:1). See, Brenneman et al., *J. Clin. Invest.*, 97:2299-2307 (1996), Glazner et al., *Anat. Embryol.* (In press), Brenneman et al., *J. Pharm. Exp. Ther.*, 285:619-27 (1998), Gozes & Brenneman, *J. Mol. Neurosci.* 7:235-244 (1996), and Gozes et al., *Dev. Brain Res.* 99:167-175 (1997), all of which are herein incorporated by reference. Unless indicated as otherwise, "SAL" refers to a peptide having an amino acid sequence of Ser-Ala-Leu-Leu-Arg-Ser-Ile-Pro-Ala (SEQ ID NO:1), not a peptide having an amino acid sequence of Ser-Ala-Leu. A full length amino acid sequence of ADNF I can be found in WO 96/11948, herein incorporated by reference in its entirety.

The terms "ADNF III" and "ADNP" refer to an activity dependent neurotrophic factor polypeptide having a predicted molecular weight of about 95 kDa (about 828 amino acid residues) and a pI of about 5.99. As described above, ADNF III polypeptides have an active site comprising an amino acid sequence of Asn-Ala-Pro-Val-Ser-Ile-Pro-Gln (also referred to as "NAPVSIPQ" or "NAP"; SEQ ID NO:2). See, Bassan et al., *J. Neurochem.* 72:1283-1293 (1999), incorporated herein by reference. Unless indicated as otherwise, "NAP" refers to a peptide having an amino acid sequence of Asn-Ala-Pro-Val-Ser-Ile-Pro-Gln (SEQ ID NO:2), not a peptide having an amino acid sequence of Asn-Ala-Pro. Full length sequences of ADNF III can be found in WO 98/35042 and WO 00/27875.

The phrase "improving learning and/or memory" refers to an improvement or enhancement of at least one parameter that indicates learning and memory. Improvement or enhancement is change of a parameter by at least 10%, optionally at least about 20%, at least about 30%, at least about 40%, at least about 50%, at least about 60%, at least about 70%, at least about 80%, at least about 90%, at least about 100%, at least about 150%, at least about 200%, etc. The improvement of learning and memory can be measured by any methods known in the art. For example, ADNF polypeptides that improve learning and memory can be screened using Morris water maze (see, e.g., materials and methods section). See, also, Gozes et al., *Proc. Natl. Acad. Sci. USA* 93:427-432 (1996). Memory and learning can also be screened using any of the methods described herein or other methods that are well known to those of skill in the art, e.g., the Randt Memory Test, the Wechler Memory Scale, the Forward Digit Span test, or the California Verbal Learning Test.

The term "memory" includes all medical classifications of memory, e.g., sensory, immediate, recent and remote, as well as terms used in psychology, such as reference memory, which refers to information gained from previous experience, either recent or remote (see, e.g., *Harrison's Principles of Internal Medicine*, volume 1, pp. 142-150 (Fauci et al., eds., 1988).

Pathologies or neuropathologies that would benefit from therapeutic and diagnostic applications of this invention include, for example, the following:

diseases of central motor systems including degenerative conditions affecting the basal ganglia (Huntington's disease, Wilson's disease, striatonigral degeneration, corticobasal ganglionic degeneration), Tourette's syndrome, Parkinson's disease, progressive supranuclear palsy, progressive bulbar palsy, familial spastic paraplegia, spinomuscular atrophy, ALS and variants thereof, dentatorubral atrophy, olivo-pontocerebellar atrophy, paraneoplastic cerebellar degeneration, and dopamine toxicity;

diseases affecting sensory neurons such as Friedreich's ataxia, diabetes, peripheral neuropathy, retinal neuronal degeneration;

diseases of limbic and cortical systems such as cerebral amyloidosis, Pick's atrophy, Retts syndrome;

neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration;

pathologies associated with developmental retardation and learning impairments, and Down's syndrome, and oxidative stress induced neuronal death;

pathologies arising with aging and chronic alcohol or drug abuse including, for example, with alcoholism the degeneration of neurons in locus coeruleus, cerebellum, cholinergic basal forebrain; with aging degeneration of cerebellar neurons and cortical neurons leading to cognitive and motor impairments; and with chronic amphetamine abuse degeneration of basal ganglia neurons leading to motor impairments;

pathological changes resulting from focal trauma such as stroke, focal ischemia, vascular insufficiency, hypoxic-ischemic encephalopathy, hyperglycemia, hypoglycemia, closed head trauma, or direct trauma;

pathologies arising as a negative side-effect of therapeutic drugs and treatments (e.g., degeneration of cingulate and entorhinal cortex neurons in response to anticonvulsant doses of antagonists of the NMDA class of glutamate receptor).

The term "spatial learning" refers to learning about one's environment and requires knowledge of what objects are where. It also relates to learning about and using information about relationships between multiple cues in environment. Spatial learning in animals can be tested by allowing animals to learn locations of rewards and to use spatial cues for remembering the locations. For example, spatial learning can be tested using a radial arm maze (i.e., learning which arm has food) a Morris water maze (i.e., learning where the platform is). To perform these tasks, animals use cues from test room (positions of objects, odors, etc.). In human, spatial learning can also be tested. For example, a subject can be asked to draw a picture, and then the picture is taken away. The subject is then asked to draw the same picture from memory. The latter picture drawn by the subject reflects a degree of spatial learning in the subject.

The term "subject" refers to any mammal, in particular human, at any stage of life. For example, the subject can refer to an embryo, a fetus, a baby, a child, an adolescent or an adult.

A "normal" subject or a subject having "normal mental capacity" refers to a subject whose intellectual functioning level is around or above average (e.g. having an IQ above 75). A "normal" subject can also refer to a subject, such as a fetus, who does not appear to have any mental impairment (e.g., according to an amniocentesis test) and/or has no risk factors (e.g., family history of mental retardation or a mother who consumed alcohol in excessive amount during pregnancy to cause fetal alcohol syndrome in the fetus).

A subject is considered to have "mental retardation" based on the following three criteria: intellectual functioning level (IQ) is below 70-75; significant limitations exist in two or more adaptive skill areas; and the condition is present from childhood (defined as age 18 or less) (AAMR, 1992). Adaptive skill areas are those daily living skills needed to live, work and play in the community. They include communication, self-care, home living, social skills, leisure, health and safety, self-direction, functional academics (reading, writing, basic math), community use and work. See, www.thearc.org/faqs/mrqa.html.

The term "Down's syndrome" is a chromosome disorder and occurs when, instead of the normal complement of 2 copies of chromosome 21, there is a whole, or sometimes part of an additional chromosome 21.

The term "contacting" is used herein interchangeably with the following: combined with, added to, mixed with, passed over, incubated with, flowed over, etc. Moreover, the ADNF polypeptides or nucleic acids encoding them of the present invention can be "administered" by any conventional method such as, for example, parenteral, oral, topical, and inhalation routes. In presently preferred embodiments, parenteral and nasal inhalation routes are employed.

"An amount sufficient" or "an effective amount" is that amount of a given ADNF polypeptide that improves performance (e.g., learning and/or memory). For example, in the context of improving learning and memory, "an amount sufficient" or "an effective amount" is that amount of a given ADNF polypeptide that reduces the latency in finding a platform in a watermaze test, either in the first daily test (indicative of reference memory) or in the second daily test (indicative of short term memory). The dosing range can vary depending on the ADNF polypeptide used, the route of administration and the potency of the particular ADNF polypeptide, but can readily be determined using the foregoing assays.

The terms "isolated," "purified," or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated ADNF nucleic acid is separated from open reading frames that flank the ADNF gene and encode proteins other than ADNF. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

The terms "polypeptide," "peptide," and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers.

The term "amino acid" refers to naturally occurring amino acids, amino acid analogs, and amino acid mimetics that function in a manner similar to the naturally occurring and analog amino acids. Naturally occurring amino acids are those encoded by the genetic code, as well as those amino acids that are later modified, e.g., hydroxyproline, -carboxyglutamate, and O-phosphoserine. Amino acid analogs refers to synthetic amino acids that have the same basic chemical structure as a naturally occurring amino acid, i.e., an a carbon that is bound to a hydrogen, a carboxyl group, an amino group, and an R group (e.g., homoserine, norleucine, methionine sulfoxide, methionine methyl sulfonium). Such analogs have modified R groups (e.g. norleucine) or modified peptide backbones, but retain the same basic chemical structure as a naturally occurring amino acid. Both naturally occurring and analog amino acids can be made synthetically. Amino acid mimetics refer to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (1), Leucine (L), Valine (V); and
8) Phenylalanine (F), Tyrosine (Y), Tryptophan (W).

(see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides (i.e., 70% identity) that are the same, when compared and aligned for maximum correspondence over a comparison window, as measured using one of the following sequence comparison algorithms or by manual alignment and visual inspection. Such sequences are then said to be "substantially identical." This definition also refers to the complement of a test sequence. Preferably, the percent identity exists over a region of the sequence that is at least about 25 amino acids in length, more preferably over a region that is 50 or 100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

DETAILED DESCRIPTION OF THE INVENTION AND PREFERRED EMBODIMENTS

Methods for Improving Performance

The present invention provides a method for improving performance (e.g., learning and/or memory) in a subject. The method comprises administering to the subject, either prenatally or postnatally, an ADNF polypeptide in an amount sufficient to improve post natal performance. In particular, prenatal administration can improve spatial learning in a subject. Candidate subjects who can benefit from such post or prenatal treatment, ADNF polypeptides that can be administered, timing and modes of administration, tests to assess improvement in learning and memory, and methods for producing ADNF polypeptides are described in detail below.

Candidate Subjects for Treatment with ADNF Polypeptides

The prenatal and postnatal treatment with ADNF polypeptides has applications in many types of subjects. For example, normal subjects can benefit from the prenatal treatment of ADNF polypeptides in terms of improving their learning and memory. A normal subject or a subject with normal mental capacity refers to those whose intellectual functioning level, even without the prenatal treatment with ADNF polypeptides, is around or above average (e.g., having an IQ over 75). In the context of a fetus, a normal subject can refer to a subject who does not appear to have any mental impairment (e.g., according to an amniocentesis test) and/or risk factors for mental retardation (e.g., family history of mental retardation or a mother who consumed enough alcohol during pregnancy to cause fetal alcohol syndrome in the subject). A mother who wishes her unborn embryo or fetus to have enhanced capacity for learning and memory can be administered with ADNF polypeptides while the embryo or fetus is in utero.

Moreover, the present methods can benefit subjects whose mental ability is compromised. For example, if a fetus is diagnosed as likely having mental retardation or Down's syndrome, the fetus can be treated in utero with ADNF polypeptides so that postnatal learning and memory can be ameliorated. In a preferred embodiment, mental retardation is not caused by maternal consumption of alcohol during pregnancy. In other words, a candidate subject who has mental retardation does not have fetal alcohol syndrome (which can include a condition of usually mild to moderate, but occasionally severe, mental retardation or learning disabilities).

Severe mental retardation (defined as an IQ of 50 or less) often originates from genetic disorders. These include, e.g., Down's syndrome, fragile X syndrome, Klinefelter's syndrome, Prader-Willi syndrome and cri du chat syndrome. Many of these conditions can be diagnosed with a prenatal genetic test. For example, genetic disorders can be tested by an amniocentesis test which is typically performed between 14 and 18 weeks of pregnancy or by a chorionic villus sampling which is performed between 9 and 12 weeks of pregnancy. Prenatal treatment of the fetus with ADNF polypeptides can benefit their postnatal learning and memory.

Even without a prenatal diagnosis of genetic disorders that cause mental retardation, ADNF polypeptides can be prophylactically administered to the fetus in certain circumstances. For example, if the subject has a family history of mental retardation, the subject can be prenatally treated with ADNF polypeptides. In another example, if the subject is at a higher risk of being born with mental retardation due to infections such as rubella, meningitis, CMV, etc., the subject can be prenatally treated with ADNF polypeptides. In another example, the subject is at a higher risk of being born with certain genetic disorders, such as Down's syndrome, when the mother is older (e.g., 35 years or older). Prophylactic prenatal treatment with ADNF polypeptides can ameliorate the subject's capacity for learning and memory.

In other embodiments, the subject can be treated later in life, for example, to improve short term learning and memory. For example, certain memory and learning disorders, such as Alzheimer's disease, may not be apparent until later in life. Other conditions that can be treated using postnatal administration of ADNF polypeptides include, neuropathology; sensory-motor problems; improving the performance of subjects impaired in cognitive tasks; improving the performance of subjects with memory deficiencies; improving the performance of normal subjects; and the like. Accordingly, embodiments of the invention in suitable formulations, can be employed for decreasing the amount of time needed to learn a cognitive, motor or perceptual task. Alternatively, invention compounds, in suitable formulations, can be employed for increasing the time for which cognitive, motor or perceptual tasks are retained. As another alternative, embodiments of the invention in suitable formulations, can be employed for decreasing the quantity and/or severity of errors made in recalling a cognitive, motor or perceptual task. Such treatment may prove especially advantageous in individuals who have suffered injury to the nervous system, or who have endured disease of the nervous system. Moreover, ADNF polypeptides can be administered to normal subjects to improve their performance (e.g., learning and memory). ADNF polypeptides can be particularly useful for an aged population in which capacity for memory (e.g. short term) has generally declined.

ADNF Polypeptides

Any suitable ADNF polypeptides can be administered in embodiments of the invention. For example, an ADNF polypeptide can be an ADNF I polypeptide, an ADNF III polypeptide, or a mixture thereof. In some embodiments, ADNF polypeptides may comprise all L-amino acids, all D-amino acids, or a combination thereof. When ADNF polypeptides are to be orally administered, preferably an ADNF polypeptide comprises at least one D-amino acid within its active core site, more preferably at the N-terminus and/or the C-terminus of the active core site, and even more preferably at the entire active core site or over the length of the molecule. Alternatively, the D-amino acid can be at any suitable position in the polypeptide sequence. Since D-enatiomers of polypeptides are enzymatically more stable than their L-enatiomers, particularly in the gastrointestinal tract, an ADNF polypeptide comprising D-amino acids are particularly useful for oral administration.

In one aspect, the method comprises administering an ADNF I polypeptide that comprises an active core site having the following amino acid sequence: Ser-Ala-Leu-Leu-Arg-Ser-Ile-Pro-Ala (SEQ ID NO:1). In one embodiment, the ADNF I polypeptide consists of an active core site that has an amino acid sequence of Ser-Ala-Leu-Leu-Arg-Ser-Ile-Pro-Ala (SEQ ID NO:1). In another embodiment, the ADNF I polypeptide can comprise additional amino acids at the N-terminus and/or at the C-terminus of the active core site. For example, the ADNF I polypeptide can comprise up to 40 amino acids at the N-terminus and/or the C-terminus of the active core site. In another example, the ADNF I polypeptide can comprise up to 20 amino acids at the N-terminus and/or the C-terminus of the active core site. In yet another example, the ADNF I polypeptide can comprise up to 10 amino acids at the N-terminus and/or the C- terminus of the active core site. In yet another embodiment, the ADNF I polypeptide can be a fill length ADNF I polypeptide.

In another aspect, the method comprises administering to the subject an ADNF III polypeptide that comprises an active core site having the following amino acid sequence: Asn-Ala-Pro-Val-Ser-Ile-Pro-Gln(SEQ ID NO:2). In one embodiment, the ADNF I polypeptide consists of an active core site that has an amino acid sequence of Asn-Ala-Pro-Val-Ser-Ile-Pro-Gln (SEQ ID NO:2). In another embodiment, the ADNF III polypeptide can comprise additional amino acids at the N-terminus and/or at the C-terminus of the active core site. For example, the ADNF III polypeptide can comprise up to 40 amino acids at the N-terminus and/or the C- terminus of the active core site. In another example, the ADNF III polypeptide can comprise up to 20 amino acids at the N-terminus and/or the C-terminus of the active core site. In yet another example, the ADNF III polypeptide can comprise up to 10 amino acids at the N-terminus and/or the C-terminus of the active core site. In yet another embodiment, the ADNF III polypeptide can be a full length ADNF III polypeptide.

In a preferred embodiment, the ADNF I polypeptide comprises an amino acid sequence of $(R_1)_x$-Ser-Ala-Leu-Leu-Arg-Ser-Ile-Pro-Ala-$(R^2)_y$ (SEQ ID NO:3), and the ADNF III polypeptide comprises an amino acid sequence of $(R_3)_w$-Asn-Ala-Pro-Val-Ser-Ile-Pro-Gln-$(R^4)_z$ (SEQ ID NO:13).

In the above formula, each of $R^1$, $R^2$, $R^3$, and $R^4$, if present, is an amino acid sequence comprising from 1 to about 40 amino acids wherein each amino acid is independently selected. The term "independently selected" is used herein to indicate that the amino acids making up, for example, the amino acid sequence $R^1$ may be identical or different (e.g., all of the amino acids in the amino acid sequence may be threonine, etc.). Moreover, as previously explained, the amino acids making up the amino acid sequence $R^1$ may be either naturally occurring amino acids, or known analogues of natural amino acids that functions in a manner similar to the naturally occurring amino acids (i.e., amino acid mimetics). This discussion pertaining to $R^1$ is fully applicable to $R^2$, $R^3$, and $R^4$.

Within the above formula for the ADNF I polypeptide, x and y are independently selected and are equal to zero or one. The term independently selected is used herein to indicate that x and y may be identical or different. For example, x and y may both be zero or, alternatively, x and y may both be one. In addition, x may be zero and y may be one or, alternatively, x may be one and y may be zero. Moreover, if x and y are both one, the amino acid sequences $R^1$ and $R^2$ may be the same or different. As such, the amino acid sequences $R^1$ and $R^2$ are independently selected. If $R^1$ and $R^2$ are the same, they are identical in terms of both chain length and amino acid composition. For example, both $R^1$ and $R^2$ may be Val-leu-Gly-Gly-Gly. If $R^1$ and $R^2$ are different, they can differ from one another in terms of chain length and/or amino acid composition and/or order of amino acids in the amino acids sequences. For example, $R^1$ may be Val-Leu-Gly-Gly-Gly (SEQ ID NO:4), whereas $R^2$ may be Val-Leu-Gly-Gly. (SEQ ID NO:5). Alternatively, $R^1$ may be Val-Leu-Gly-Gly-Gly(SEQ ID NO:4), whereas $R^2$ may be Val-Leu-Gly-Gly-Val (SEQ ID NO:6). Alternatively, $R^1$ may be Val-Leu-Gly-Gly-Gly (SEQ ID NO:4), whereas $R^2$ may be Gly-Val-Leu-Gly-Gly(SEQ ID NO:7).

Similarly, w and z are independently selected and are equal to zero or one within the above formula for the ADNF III polypeptide. The term independently selected is used herein to indicate that w and z may be identical or different. For example, w and z may both be zero or, alternatively, w and z may both be one. In addition, w may be zero and z may be one or, alternatively, w may be one and z may be zero. Moreover, if w and z are both one, the amino acid sequences $R^3$ and $R^4$ may be the same or different. As such, the amino acid sequences $R^3$ and $R^4$ are independently selected. If $R^3$ and $R^4$ are the same, they are identical in terms of both chain length and amino acid composition. For example, both $R^3$ and $R^4$ may be Leu-Gly-Leu-Gly-Gly (SEQ ID NO:8). If $R^3$ and $R^4$ are different, they can differ from one another in terms of chain length and/or amino acid composition and/or order of amino acids in the amino acids sequences. For example, $R^3$ may be Leu-Gly-Leu-Gly-Gly(SEQ ID NO:8), whereas $R^4$ may be Leu-Gly-Leu-Gly(SEQ ID NO:9). Alternatively, $R^3$ may be Leu-Gly-Leu-Gly-Gly (SEQ ID NO:8), whereas $R^4$ may be Leu-Gly-Leu-Gly-Leu (SEQ ID NO:10).

Within the scope, certain ADNF I and ADNF III polypeptides are preferred, namely those in which x, y, w, and z are all zero (i.e., SALLRSIPA; SEQ ID NO:1 and NAPVSIPQ; SEQ ID NO:2, respectively). Equally preferred are ADNF I polypeptides in which x is one; $R^1$ is Val-Leu-Gly-Gly-Gly (SEQ ID NO:4; and y is zero. Also equally preferred are ADNF I polypeptides in which x is one; $R^1$ is Val-Glu-Glu-Gly-Ile-Val-Leu-Gly-Gly-Gly (SEQ ID NO:11); and y is zero. Also equally preferred are ADNF III polypeptides in which w is one; $R^3$ is Gly-Gly; and z is zero. Also equally preferred are ADNF III polypeptides in which w is one; $R^3$ is Leu-Gly-Gly; z is one; and $R^4$ is Gln-Ser. Also equally preferred are ADNF III polypeptides in which w is one; $R^3$ is Leu-Gly-Leu-Gly-Gly-(SEQ ID NO:8); z is one; and $R^4$ is Gln-Ser. Also equally preferred are ADNF III polypeptides in which w is one; $R^3$ is Ser-Val-Arg-Leu-Gly-Leu-Gly-Gly (SEQ ID NO:12); z is one; and $R^4$ is Gln-Ser. Additional amino acids can be added to both the N-terminus and the C-terminus of these active sites (SALLRSIPA; SEQ ID NO:1 or NAPVSIPQ; SEQ ID NO:2) without loss of biological activity as evidenced by the fact that the intact ADNF I or ADNF III growth factors exhibit extraordinary biological activity. See, U.S. Ser. No. 08/324,297, filed Oct. 17, 1994 (also published as WO96/11948) for the description of ADNF I polypeptides; and U.S. Ser. No. 60/037,404 filed Feb. 27, 1997 and U.S. Ser. No. 60/059,621 filed, Sep. 23, 1997 (also published as WO98/35042) for the description of ADNF III polypeptides, all of which are incorporated herein by reference.

In yet another aspect the method comprises administering to the subject a mixture of an ADNF I polypeptide and an ADNF III polypeptide. Any one or more of the ADNF I polypeptides described herein can be mixed with any one or more of the ADNF III polypeptides described herein. A mixture of an ADNF I polypepdde and an ADNF Ill polypeptide can be a blend of two or more of these polypeptides. A mixture of an ADNF I polypeptide and an ADNF III polypeptide can also refer to one or more of ADNF I polypeptides that are coupled (directly or indirectly) to one or more of ADNF III polypeptides. For example an ADNF I polypeptide can be covalently linked to an ADNF III polypeptide. A mixture of ADNF I polypeptides and ADNF III polypeptides can be prepared as a single composition and can be administered to a subject. Alternatively, an ADNF I polypeptide and an ADNF III polypeptide can be prepared as separate compositions. The separate compositions can then be administered simultaneously or sequentially to the subject. Furthermore, different proportions of an ADNF I polypeptide and an ADNF III polypeptide can be administered to a subject. For example, the subject can be administered with ADNF polypeptides, wherein the ratio of an ADNF I polypeptide and an ADNF III polypeptide can be in the range of 1:100 to 100:1, 1:10 to 10:1, or 1:2 to 2:1.

In yet another aspect, other ADNF polypeptide (including their alleles, polymorphic variants, species homologs and subsequences thereof) can be used to enhance performance.

Various parameters can be measured to determine if an ADNF polypeptide or a mixture of ADNF polypeptides improves performance of a subject. For example, the degree of learning deficits can be compared between the control (e.g. untreated with ADNF polypeptides) and a group pretreated with ADNF polypeptides. Learning deficits can be assessed using, for example, a Morris water maze (see, e.g., the Example section). If any one or more of these parameters are changed for the group treated with ADNF polypeptides by, e.g., about 10%, optionally at least about 20%, at least about 30%, at least about 40%, at least about 50%, at least about 60%, at least about 70%, at least about 80%, at least about 90%, at least about 100%, at least about 150%, at least about 200%, etc., compared to control, then these ADNF polypeptides can be advantageously used in the present invention.

Administration and Pharmaceutical Compositions

ADNF polypeptides and nucleic acids encoding ADNF polypeptides can be prenatally or postnatally administered to the subject using any suitable methods known in the art. For example, ADNF polypeptides or nucleic acids can be formulated as pharmaceutical compositions with a pharmaceutically acceptable diluent, carrier or excipient. Suitable formulations for use in the present invention are found in *Remington's Pharmaceutical Sciences* (17th ed. 1985)), which is incorporated herein by reference. A brief review of methods for drug delivery is also described in, e.g., Langer, *Science* 249: 1527-1533 (1990), which is incorporated herein by reference. In addition, the pharmaceutical compositions comprising peptides and proteins are described in, e.g., *Therapeutic Peptides and Proteins Formulations, Processing, and Delivery Systems*, by Banga, Technomic Publishing Company, Inc., Lancaster, Pa. (1995).

In one embodiment, ADNF polypeptides are formulated for oral administration, e.g., to the subject, or for prenatal administration, to the subject's mother. In this embodiment, it is preferred that ADNF polypeptides comprising all D-amino acids are used. A pharmaceutically acceptable nontoxic composition is formed by incorporating any of normally employed excipients, and generally 10-95% of active ingredient and more preferably at a concentration of 25%-75%. Furthermore, to improve oral absorption of ADNF polypeptides, various carrier systems, such as nanoparticles, microparticles, liposomes, phospholipids, emulsions, erythrocytes, etc. can be used. The oral agents comprising ADNF polypeptides of the invention can be in any suitable form for oral administration, such as liquid, tablets, capsules, or the like. The oral formulations can be further coated or treated to prevent or reduce dissolution in stomach. See, e.g., *Therapeutic Peptides and Proteins, Formulation, Processing, and Delivery Systems*, by A. K. Banga, Technomic Publishing Company, Inc., 1995.

Furthermore, the ADNF polypeptides can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that comprise a solution of a mixture of ADNF polypeptides, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc. In one embodiment, a nucleic acid encoding an ADNF polypeptide is administered as a naked DNA.

For aerosol administration, ADNF polypeptides are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intrinasal delivery.

For solid compositions, conventional nontoxic solid carriers may be used. Solid carriers include, for example, pharmaceutical grades of mannitol, lactose, starch, magnesium stearate, sodium saccharin, talcum, cellulose, glucose, sucrose, magnesium carbonate, and the like.

The present invention also provides for therapeutic compositions or medicaments comprising a mixture of one or more of the ADNF I and ADNF III polypeptides described herein above in mixture with a pharmaceutically acceptable excipient, wherein the amount of a mixture the ADNF I and ADNF III polypeptide is sufficient to provide a desirable therapeutic effect.

Small polypeptides including SALLRSIPA (SEQ ID NO:1) and NAPVSIPQ (SEQ ID NO:2) cross the blood brain barrier. For longer polypeptides that do not the cross blood brain barrier, methods of administering proteins to the brain are well known. For example, proteins, polypeptides, other compounds and cells can be delivered to the mammalian brain via intracerebroventricular (ICV) injection or via a cannula (see, e.g., Motta & Martini, *Proc. Soc. Exp. Biol. Med.* 168:62-64 (1981); Peterson et al., *Biochem. Pharamacol.* 31:2807-2810 (1982); Rzepczynski et al., *Metab. Brain Dis.* 3:211-216 (1988); Leibowitz et al., *Brain Res. Bull.* 21:905-912 (1988); Sramka et al., *Stereotact. Funct. Neurosurg.* 58:79-83 (1992); Peng et al., *Brain Res.* 632:57-67 (1993); Chem et al., *Exp. Neurol.* 125:72-81 (1994); Nikkhah et al., *Neuroscience* 63:57-72 (1994); Anderson et al., *J. Comp. Neurol.* 357:296-317 (1995); and Brecknell & Fawcett, *Exp. Neurol.* 138:338-344 (1996)). In particular, cannulas can be used to administer neurotrophic factors to mammals (see, e.g., Motta & Martini, *Proc. Soc. Exp. Biol. Med.* 168:62-64 (1981) (neurotensin); Peng et al., *Brain Res.* 632:57-67 (1993) (NGF); Anderson et al., *J. Comp. Neurol.* 357:296-317 (1995) (BDNF, NGF, neurotrophin-3).

Alternatively, longer ADNF polypeptides that do not cross blood brain barrier can be coupled with a material which assists the ADNF polypeptide to cross the blood brain barrier and to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as ADNF polypeptides across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the hydrophobic domain of signal peptides, was found to have similar cell membrane translocation characteristics (see, e.g., Lin et al., *J. Biol. Chem.* 270:14255-14258 (1995)).

Examples of peptide sequences which can be linked to a ADNF polypeptide of the invention, for facilitating uptake of ADNF polypeptides into cells, include, but are not limited to: an 11 animo acid peptide of the tat protein of HHV (see Schwarze et al., *Science* 285:1569-1572 (1999)); a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269: 10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to ADNF polypeptides.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.*, 268:3334-3341 (1993); Perelle et al., *Infect. Immun.*, 61:5147-5156 (1993); Stenmark et al., *J. Cell Biol.* 113:1025-1032 (1991); Donnelly et al., *Proc. Nat'l Acad. Sci. USA* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *Proc. Nat'l Acad. Sci. USA* 89:10277-10281 (1992); and Novak et al., *J. Biol. Chem.* 267:17186-17193 1992)).

Such subsequences can be used to translocate ADNF polypeptides across a cell membrane. ADNF polypeptides can be conveniently fused to or derivatized with such sequences. Typically, the translocation sequence is provided as part of a fusion protein. Optionally, a linker can be used to link the ADNF polypeptides and the translocation sequence. Any suitable linker can be used, e.g., a peptide linker.

The ADNF polypeptides and nucleic acids encoding ADNF polypeptides can also be introduced into an animal cell, preferably a mammalian cell, via a liposomes and liposome derivatives such as immunoliposomes and lipid:nucleic acid complexes. The term "liposome" refers to vesicles comprised of one or more concentrically ordered lipid bilayers, which encapsulate an aqueous phase. The aqueous phase typically contains the compound to be delivered to the cell, i.e., an ADNF polypeptide.

The liposome fuses with the plasma membrane, thereby releasing the ADNF polypeptides into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, an ADNF polypeptide) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., *Proc. Nat'l Acad. Sci. USA* 84:7851 (1987); *Biochemistry* 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise an ADNF polypeptide and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., *Ann. Rev. Biophys. Bioeng.* 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, *Biochim. Biophys. Acta* 443:629-634 (1976); Fraley, et al., *Proc. Nat'l Acad. Sci. USA* 76:3348-3352 (1979); Hope et al., *Biochim. Biophys. Acta* 812:55-65 (1985); Mayer et al., *Biochim. Biophys. Acta* 858:161-168 (1986); Williams et al., *Proc. Nat'l Acad. Sci USA* 85:242-246 (1988); *Liposomes* (Ostro (ed.), 1983, Chapter 1); Hope et al., *Chem. Phys. Lip.* 40:89 (1986); Gregoriadis, *Liposome Technology* (1984) and Lasic, *Liposomes: from Physics to Applications* (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044). Standard methods for coupling targeting agents to liposomes can be used. These methods generally involve incorporation into liposomes lipid components, e.g., phosphatidylethanoiamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., *J. Biol. Chem.*, 265:16337-16342 (1990) and Leonetti et al., *Proc. Nat'l Acad. Sci. USA* 87:2448-2451 (1990).

Alternatively, nucleic acids encoding ADNF can also be used to provide a therapeutic dose of ADNF polypeptides. These nucleic acids can be inserted into any of a number of well-known vectors for the transfection of target cells and organisms. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™. Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

In therapeutic applications, a mixture of ADNF I and ADNF III polypeptides of the invention are administered to a patient in an amount sufficient to improve a subject's performance (e.g., learning and/or memory). An amount adequate to accomplish this is defined as "therapeutically effective dose." Amounts effective for this use will depend on, for example, the particular ADNF I or ADNF III polypeptide employed, the manner of administration, the weight and general state of health of the patient, and the judgment of the prescribing physician. For example, for the improvement of performance (e.g., learning and memory), an amount of ADNF I or ADNF III polypeptides falling within the range of a 1 μg to 50 μg, preferably 1 μg to 10 μg dose given intranasally once a day per mouse (e.g., in the evening) would be a therapeutically effective amount. This dose is based on the average body weight of a mouse. Therefore, an appropriate dose can be extrapolated for a human body.

ADNF polypeptides can be prenatally administered to the subject directly or indirectly through the subject's mother. ADNF polypeptides can be administered at any time during the pregnancy. Preferably, ADNF polypeptides are administered to the subject during the first trimester (i.e., first 12 weeks) of the pregnancy when organs and the nervous system of the subject are actively developing. More preferably, ADNF polypeptides are administered during the time of neural tube development (which begins around 22 days post-conception) and prior to its closure. ADNF polypeptides can be administered as a single dose, preferably during the critical period of neural tube development, or can be administered as multiple doses throughout the pregnancy.

Tests for Measuring Improved Learning and/or Memory

Various parameters can be measured to determine if ADNF polypeptides improve performance (e.g., learning and memory) in vivo. For example, the hidden platform test of the Morris water maze, which is described in the example section below, can be used to test spatial learning and memory. Generally, mice that are treated with ADNF polypeptides and control mice (that are not treated with ADNF polypeptides) are trained to escape the swimming task by learning the position of a hidden platform and climbing on it. The time it takes them to complete this task is defined as the escape latency. This test can be conducted one or more times daily for a number of days. One parameter that is indicative of improved learning and memory is the reduction in latency in escaping the swimming task by climbing onto the hidden platform (see the example section below). See, also, methods described in Gozes et al., *Proc. Natl. Acad. Sci. USA* 93:427-432 (1996), incorporated herein by reference. Animals treated with suitable ADNF polypeptides show improvement in their leaning and memory capacities compared to the controls that are not treated with ADNF polypeptides. Embodiments of the invention are not limited by examples of the test used to measure performance. Any suitable test methods can be used to measure performance, such as learning and memory.

Other methods known in the art can be used in human subjects to determine if an ADNF polypeptide or a combination of ADNF polypeptides improves performance (e.g., learning and memory) in vivo. For example, these methods include assessment of memory or learning over time by the Randt Memory Test (Randt et al., *Clin. Neuropsychol.,* 1980, 2:184), Wechsler Memory Scale (*J. Psych.* 19:87-95 (1945), Forward Digit Span test (Craik, Age Differences in Human Memory, in: *Handbook of the Psychology of Aging,* Birren, J., and Schaie, K. (Eds.), New York, Van Nostrand (1977), Mini-Mental State Exam (Folstein et al., *J. of Psych. Res.* 12:189-192 (1975), or California Verbal Learning Test (CVLT). See, also, U.S. Pat. No. 6,030,968. In these tests, factors unrelated to effects of ADNF polypeptides (e.g., anxiety, fatigue, anger, depression, confusion, or vigor) are controlled for. See, U.S. Pat. No. 5,063,206. Methods for assessing and controlling for subjective factors is known in the art and determined by such standard clinical tests such as the BECK Depression Scale, Spielberger Trait State Anxiety test, and POMS test (Profile of Mood State).

Spatial learning can also be tested in human. For example, a subject can be asked to draw a picture, and then the picture is taken away. The subject is then asked to draw the same picture from memory. The latter picture drawn by the subject reflects a degree of spatial learning in the subject.

Various parameters can be measured to determine if ADNF polypeptides improve learning and memory of a subject. For example, the degree of learning and memory improvement can be compared between the control (e.g. untreated with ADNF polypeptides) and a group pretreated with ADNF polypeptides. Learning and memory improvement can be assessed using, for example, a Morris water maze for rodents (see, e.g., the Example section) or any suitable tests such as those described above for humans. If any one or more of these parameters are changed for the group treated with ADNF polypeptides by, e.g., about 10%, optionally at least about 20%, at least about 30%, at least about 40%, at least about 50%, at least about 60%, at least about 70%, at least about 80%, at least about 90%, at least about 100%, at least about 150%, at least about 200%, etc., compared to control, then it can be said that the ADNF polypeptides improved learning and memory of the subject. Alternatively, statistical analysis using ANOVA for continuous variables, Mann-Whitney U for nonparametric data, Chi square for categorical variables or Fisher's exact test with p<0.05 is considered significant.

Methods for Production of ADNF Polypeptides

Recombinant Methods for Production of ADNF Polypeptides
 Cloning and Isolation of ADNF Nucleic Acids Several specific nucleic acids encoding ADNF polypeptides are described herein. See, also, e.g., Brenneman & Gozes, *J. Clin. Invest.* 97:2299-2307 (1996), Brenneman, *J.*

Pharm. Exp. Ther. 285:619-627 (1998), and Bassan et al., *J. Neurochem* 72:1283-1293 (1999), the teachings of which are hereby incorporated in their entirety by reference. These nucleic acids can be made using standard recombinant or synthetic techniques. Given the nucleic acids of the present invention, one of skill can construct a variety of clones containing functionally equivalent nucleic acids, such as nucleic acids that encode the same ADNF polypeptides. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Sambrook et al., *Molecular Cloning—A Laboratory Manual* (2nd ed. 1989) and *Current Protocols in Molecular Biology* (Ausubel et al., eds., 1994).

In addition, product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

The nucleic acid compositions of this invention, whether RNA, cDNA, genomic DNA or a hybrid of the various mixtures, are isolated from biological sources, such as astrocyte, neuroblastoma cells, or fibroblasts, or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA), are found in Berger, Sambrook et al. and Ausubel et al., all supra, as well as in U.S. Pat. No. 4,683,202; *PCR Protocols A Guide to Methods and Applications* (Innis et al., eds., 1990); Arnheim & Levinson (Oct. 1, 1990) *C&EN* 36-47; *The Journal Of NIH Research* 3:81-94 (1991); Kwoh et al., *Proc. Natl. Acad. Sci. USA* 86:1173 (1989); Guatelli et al., *Proc. Natl. Acad. Sci. USA* 87:1874 (1990); Lomell et al., *J. Clin. Chem* 35:1826 (1989); Landegren et al., *Science* 241:1077-1080 (1988); Van Brunt, *Biotechnology* 8:291-294 (1990); Wu & Wallace, *Gene* 4:560 (1989); Barringer et al., *Gene* 89:117 (1990); and Sooknanan & Malek, *Biotechnology* 13:563-564 (1995). Improved methods of cloning in vitro amplified nucleic acids are described in U.S. Pat. No. 5,426,039. Improved methods of amplifying large nucleic acids are summarized in Cheng et al., *Nature* 369:684-685 (1994) and the references cited therein. One of skill will appreciate that essentially any RNA can be converted into a double stranded DNA suitable for restriction digestion, PCR expansion and sequencing using reverse transcriptase and a polymerase.

Oligonucleotides for use as probes, for example, with in vitro ADNF nucleic acid amplification methods, or for use as nucleic acid probes to detect ADNF nucleic acids, are typically synthesized chemically according to the solid phase phosphoramidite triester method described by Beaucage & Caruthers, *Tetrahedron Letts.* 22(20):1859-1862 (1981), e.g., using an automated synthesizer, e.g. as described in Needham-VanDevanter et al., *Nucleic Acids Res.* 12:6159-6168 (1984). Oligonucleotides can also be custom made and ordered from a variety of commercial sources known to those of skill in the art. Purification of oligonucleotides, where necessary, is typically performed by either native acrylamide gel electrophoresis, or by anion-exchange HPLC as described in Pearson & Regnier, *J. Chrom.* 255:137-149 (1983). The sequence of the synthetic oligonucleotides can be verified using the chemical degradation method of Maxam & Gilbert, in *Methods in Enzymology* 65:499-560 (Grossman & Moldave, eds., 1980).

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, Giliman & Smith, *Gene* 8:81-97 (1979); Roberts et al., *Nature* 328:731-734 (1987); and Sambrook et al., *Molecular Cloning—A Laboratory Manual* (2nd ed. 1989)).

Recombinant Expression of ADNF Polypeptides

In one embodiment, the polypeptides, or subsequences thereof, are synthesized using recombinant nucleic acid methodology. Generally, this involves creating a nucleic acid sequence that encodes the protein, placing the nucleic acid in an expression cassette under the control of a particular promoter, expressing the protein in a host cell, isolating the expressed protein and, if required, renaturing the protein.

Once a nucleic acid encoding an ADNF polypeptide of the invention is isolated and cloned, the nucleic acid is optionally expressed in recombinantly engineered cells known to those of skill in the art. Examples of such cells include, but are not limited to, bacteria, yeast, plant, filamentous fungi, insect (especially employing baculoviral vectors) and mammalian cells. The recombinant nucleic acids are operably linked to appropriate control sequences for expression in the selected host. For *E. coli*, example control sequences include the T7, trp, or lambda promoters, a ribosome binding site and, preferably, a transcription termination signal. For eukaryotic cells, the control sequences typically include a promoter and, preferably, an enhancer derived from immunoglobulin genes, SV40, cytomegalovirus, etc., and a polyadenylation sequence, and may include splice donor and acceptor sequences.

If desired, recombinant nucleic acids can be constructed to encode a fusion polypeptide comprising an ADNF polypeptide. For example, a nucleic acid encoding an ADNF I polypeptide can be linked to a nucleic acid encoding an ADNF III polypeptide to provide a mixture of ADNF polypeptides. In another example, a nucleic acid encoding an ADNF polypeptide (e.g., an ADNF I polypeptide, an ADNF III polypeptide, or a fusion ADNF I/ADNF III polypeptide) can be linked with another nucleic acid, such as a portion of HIV tat nucleic acid, which facilitates the delivery of the ADNF III polypeptide into tissues. In yet another example, a nucleic acid encoding an ADNF polypeptide can be linked to nucleic acids that encode affinity tags to facilitate protein purification protocol. An ADNF nucleic acid and a heterologous polynucleotide sequence can be modified to facilitate their fusion and subsequent expression of fusion polypeptides. For example, the 3' stop codon of the ADNF polynucleotide sequence can be substituted with an in frame linker sequence, which may provide restriction sites and/or cleavage sites.

The plasmids of the invention can be transferred into the chosen host cell by well-known methods. Such methods include, for example, the calcium chloride transformation method for E. coli and the calcium phosphate treatment or electroporation methods for mammalian cells. Cells transformed by the plasmids can be selected by resistance to antibiotics conferred by genes contained on the plasmids, such as the amp, gpt, neo, and hyg genes.

Once expressed, the recombinant ADNF polypeptides or naturally occurring can be purified according to standard procedures of the art, including ammonium sulfate precipitation, affinity columns, column chromatography, gel electrophoresis and the like (see, e.g., Scopes, *Polypeptide Purification* (1982); Deutscher, *Methods in Enzymology Vol. 182: Guide to Polypeptide Purification* (1990)). Once purified, partially or to homogeneity as desired, the ADNF polypeptides may then be used, e.g., to improve learning and memory in a subject. See, also, e.g., Brenneman & Gozes, *J. Clin. Invest.* 97:2299-2307 (1996), Brenneman et al., *J. Pharm. Exp. Ther.* 285:619-627 (1998), and Bassan et al. *J. Neurochem* 72:1283-1293 (1999), the teachings of which are hereby incorporated in their entirety by reference Synthesis of ADNF Polypeptides In addition to the foregoing recombinant techniques, the ADNF polypeptides of the invention are optionally synthetically prepared via a wide variety of well-known techniques. Polypeptides of relatively short size are typically synthesized in solution or on a solid support in accordance with conventional techniques (see, e.g., Merrifield, *Am. Chem. Soc.* 85:2149-2154 (1963)). Various automatic synthesizers and sequencers are commercially available and can be used in accordance with known protocols (see, e.g., Stewart & Young, *Solid Phase Peptide Synthesis* (2nd ed. 1984)). Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany & Merrifield, *Solid-Phase Peptide Synthesis*; pp. 3-284 in *The Peptides: Analysis, Synthesis, Biology. Vol. 2: Special Methods in Peptide Synthesis, Part A.*; Merrifield et al., *J. Am. Chem. Soc.* 85:2149-2156 (1963); and Stewart et al., *Solid Phase Peptide Synthesis* (2nd ed. 1984).

After chemical synthesis, biological expression or purification, the polypeptide(s) may possess a conformation substantially different than the native conformations of the constituent polypeptides. In this case, it is helpful to denature and reduce the polypeptide and then to cause the polypeptide to re-fold into the preferred conformation. Methods of reducing and denaturing polypeptides and inducing re-folding are well known to those of skill in the art (see Debinsid et al., *J. Biol. Chem.* 268:14065-14070 (1993); Kreitman & Pastan, *Bioconjug. Chem.* 4:581-585 (1993); and Buchner et al., *Anal. Biochem.* 205:263-270 (1992)). Debinski et al., for example, describe the denaturation and reduction of inclusion body polypeptides in guanidine-DTE. The polypeptide is then refolded in a redox buffer containing oxidized glutathione and L-arginine.

One of skill will recognize that modifications can be made to the polypeptides without diminishing their biological activity. Some modifications may be made to facilitate the cloning, expression, or incorporation of the targeting molecule into a fusion polypeptide. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Conservative Modifications of the ADNF Nucleic Acids and Polypeptides

One of skill will appreciate that many conservative variations of the ADNF nucleic acid and polypeptide sequences provided herein yield functionally identical products. For example, due to the degeneracy of the genetic code, "silent substitutions" (i.e., substitutions of a nucleic acid sequence that do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties (see the definitions section, supra), are also readily identified as being highly similar to a disclosed amino acid sequence, or to a disclosed nucleic acid sequence that encodes an amino acid. Such conservatively substituted variations of each explicitly listed nucleic acid and amino acid sequences are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see Giliman & Smith, *Gene* 8:81-97 (1979); Roberts et al., *Nature* 328:731-734 (1987)). For example, alanine scanning can be used to determine conservatively modified variants for SALLRSIPA (SEQ ID NO:1) or NAPVSIPQ (SEQ ID NO:2) (i.e., by substituting each amino acid one by one with an alanine or other small neutral amino acid and assay for activity as described herein).

Polypeptide sequences can also be altered by changing the corresponding nucleic acid sequence and expressing the polypeptide. Polypeptide sequences are also optionally generated synthetically using commercially available peptide synthesizers to produce any desired polypeptide (see, Merrifield, supra, and Stewart & Young, supra).

More particularly, it will be readily apparent to those of ordinary skill in the art that the ADNF polypeptides of the present invention can readily be screened for their performance enhancing effect using various assays (e.g., Morris watermaze assay).

Using these assays, one of ordinary skill in the art can readily prepare a large number of ADNF polypeptides in accordance with the teachings of the present invention and, in turn, screen them using the foregoing assay to find ADNF polypeptides, in addition to those set forth herein, which possess the neuroprotective/neurotrophic activity of the intact ADNF growth factor. For instance, using ADNF III-8 (i.e., Asn-Ala-Pro-Val-Ser-Ile-Pro-Gln;(SEQ ID NO:2) as a starting point, one can systematically add, for example, Gly-, Gly-Gly-, Leu-Gly-Gly- to the N-terminus of ADNF III-8 and, in turn, screen each of these ADNF III polypeptides in the foregoing assay to determine whether they possess neuroprotective/neurotrophic activity. In doing so, it will be found that additional amino acids can be added to both the N-terminus and the C-terminus of the newly discovered active site, i.e., Asn-Ala-Pro-Val-Ser-Ile-Pro-Gln (SEQ ID NO:2), without loss of biological activity as evidenced by the fact that the intact ADNF III growth factor exhibits extraordinary biological activity. This discussion also applies to ADNF I polypeptides.

EXAMPLES

Example I

Enhanced Learning and/or Memory After Postnatal Administration of an ADNF Polypeptide Example I describes properties of the ADNF polypeptides, such as SALLRSIPA ("ADNF-9"; SEQ ID NO:1), derived from ADNF I, and NAPVSIPQ ("NAP"; SEQ ID NO:2), derived from ADNF-III or ADNF, in control animals or animals exposed to the cholinotoxin, ethylcholine aziridium (AF64A), a blocker of choline uptake (Fisher et al., *Neurosci. Lett.* 102:325-331 (1989)). An intact cholinergic system is required for normal brain function, whereas Alzheimer's disease is associated with the death of cholinergic cells (Brumback and Leech, 1994). Thus, rats treated with AF64A provide an accepted model for testing in vivo efficacy of drugs that protect against cognitive impairments, that may result from cholinotoxicity (Fisher et al., *Neurosci. Lett.* 102:325-331 (1989); Gozes et al., *Proc. Natl. Acad Sci. U.S.A.* 93:427432 (1996); Gozes et al., *Proc. Nati. Acad. Sci. U.S.A.* 96:4143-4148 (1999)). The experiments described below show postnatal intranasal administration of ADNF polypeptides, such as ADNF-9 and NAP, provided neuroprotection against short-term memory loss associated with AF64A cholinotoxicity. The experiments also describe how ADNF polypeptides can enhance learning and memory of control animals.

Materials and Methods

Animals

Male Wistar rats (300-350 g, Harlan Laboratories, Jerusalem, Israel) were utilized for the cholinotoxicity assays.

Peptide Synthesis

Peptides were synthesized utilizing solid—phase technology and purified to homogeneity by high performance liquid chromatography (HPLC; Gozes et al., *Proc. Nati. Acad. Sci. U.S.A.* 96:4143-4148 (1999)). Purity and identity was ascertained using amino acid analysis and electrospray ionization mass spectrometry (Micromass, Manchester, U.K.). Additional peptides were purchased from Peptide Technologies, Bethesda, Md., USA.

Cholinotoxicity in Rats and Assessment of Short-Term Spatial Memory in a Water Maze Rats were subjected to two daily tests in a water maze, including a hidden platform (Morris, R., *J. Neurosci. Methods* 11:47-60 (1984); Gordon et al., *Neurosci. Lett.* 199:1-4 (1995); Gozes et al., *J Neurobiol.* 33:329-342. (1997a)). Every day for the first test, both the platform and the animal were situated in a new location with regards to the pool (with the pool being immobile).

The experiment was performed as follows: the animal was positioned on the platform for 0.5 min., then placed in the water. The time required to reach the platform (indicative of learning and intact reference memory) was measured (first test). After 0.5 minute on the platform, the animal was placed back in the water (in the previous position) for an additional second test and search for the hidden platform (retained in the previous position). The time required to reach the platform in the second trial was recorded, indicative of short-term (working) memory. Animals were tested for four days to eliminate random memory defective animals.

The best performers were injected i.c.v. at a rate of 0.21µ/min. with AF64A (Sigma RBI, Saint Louis, Mo., USA, 3 nmol/2 µl/side); control animals received an injection of saline (Gozes et al., *Proc. Nati. Acad Sci. U.S.A.* 93:427432 (1996)). Animals were allowed to recover for one week, followed by daily exposure to intranasal administration of 40 µl of 5% Sefsol (Sigma, Rehovot, Israel) and 20% isopropanol (control) or containing 1 µg peptide (experimental) (Gozes et al., *Proc. Nati. Acad Sci. US.A.* 93:427-432 (1996)).

After a week of peptide treatment, the animals were subjected to two daily tests in the water maze (as above). During the test-period, animals were also given an intranasal administration of peptide or vehicle (carrier) an hour before the daily tests. To avoid bias related to changes in motor activity in the various treatment groups, a probe trial test that assessed spatial memory was also utilized as follows. After four days of training and testing, the platform was removed and on day 5 the animals were subjected to swimming in the pool (120 sec) without the platform; in these experiments, the time spent in the quadrant of the pool where the platform used to be was recorded. Measurements were performed using the HVS video tracking system (HVS Image Ltd. Hampton, UK).

Biodistribution Following Intranasal Administration

NAP (M.W. 824.9) was synthesized to include hydroprolines and those were exchanged to produce [$^3$H]-labeled peptide (NAP, propyl 3-3,4-[$^3$H], American Radiolabeled Chemicals Inc. St. Louis, Mo., USA). The specific activity was 50 Ci/mmol. The purity and identity of NAP was ascertained using high performance liquid chromatography (HPLC) Zorbax SB-C18 (250×4.6 mm) 5 µm, and elution with a 5-25% methanol gradient in 0.1% trifluoroacetic acid over 20 minutes and detection by UV at 220 nm and [$^3$H] detector β-Ram. Two and half microliter of a solution containing 1 mCi/ml were applied to each nostril of a (200-300 g) male Wistar rat. At designated time points, rats were sacrificed and tissues solubilized (100 mg in one ml Luma Solve, Lumac by., Landgraaf, Netherlands, Netherlands) at 55° C. for 12 hours. Radioactivity was determined following the addition of Optiflour (10 ml/100 mg, Packard, Groningen, Netherlands) in a beta scintillation counter.

For determination of intact NAP in the brain, cortical tissue was homogenized with phosphate buffered saline (PBS) at 4° C. (100 mg/1 ml) and the homogenate was submitted to a 10,000 g centrifugation (10 min.) at 4° C. The resulting supernatant was frozen at −80° C. and further subjected to HPLC (RP-18, Merck, 250×4 mm; 5 µm), employing a linear gradient established between 35% acetonitrile and 75% acetonitrile in water containing 0.1% trifluoroacetic acid (Gozes et al., *Proc. Nati. Acad. Sci. U.S.A.* 96:4143-4148 (1999)).

Measurements of Cholinergic Activity

Choline acetyltransferase (ChAT) activity was measured according to published procedure (Fonnum, 1975) as before (Gozes et al., *J Neurobiol.* 33:329-342. (1997a)). At the termination of the behavioral experiment animals were sacrificed and brains (cerebral cortex) dissected and processed as before (Gozes et al., *J Neurobiol.* 33:329-342. (1997a)). Comparisons were made among controls, AF64A-treated and AF64A+peptide-treated animals.

Statistical Analysis

Statistical tests employed ANOVA one way analysis of variance with all pairwise multiple comparison procedures (Student-Newman-Keuls Method).

Results

Intranasal Administration of ADNF-9 Protects Against Short-Term Memory Loss Associated with AF64A-Treatment In Vivo As ADNF-9 is a short hydrophobic peptide, the possibility that it will affect brain functions was tested through intranasal administration. Assessments of spatial learning and memory were performed in a water maze, by measurements of the time required to find a hidden platform. Two daily tests were performed. The platform location and the animal's starting point were held constant within each pair of daily trials, but the location of the platform and the animal's starting point were changed every day.

Figure 1B:
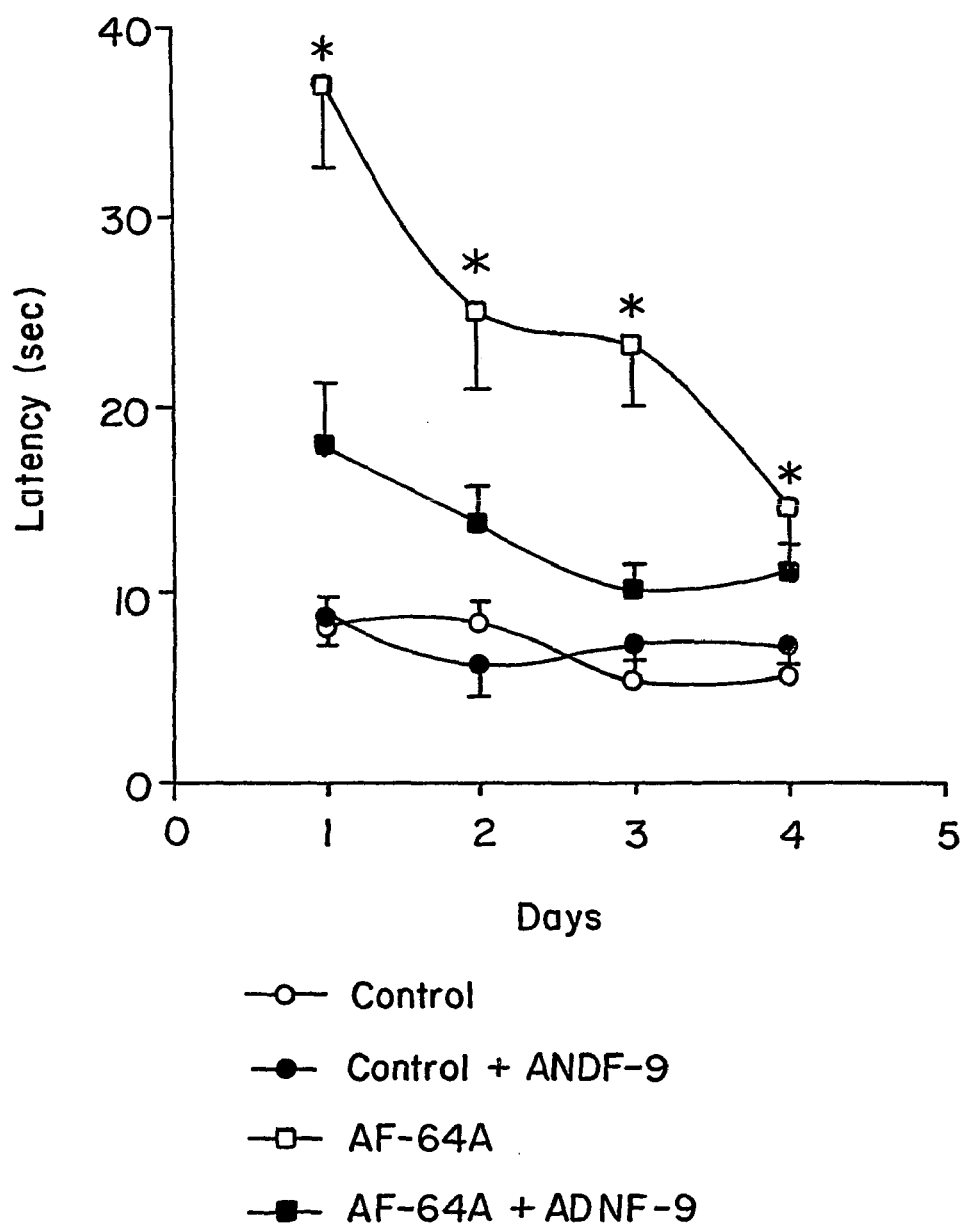

In the first daily test, indicative of reference memory, the AF64A-treated animals were retarded in comparison to control animals as was obvious on the second test day ($p<0.016$). Treatment with ADNF-9 resulted in an apparent insignificant improvement (FIG. 1A). In contrast, in the second daily test (indicative of intact short-term memory (Gordon et al., 1995)), AF64A-treated animals were markedly retarded ($p<0.001$ on all experimental days) and ADNF-9-AF64A-treated animals exhibited significant improvements and reduced latencies throughout the experiment (FIG. 1B, $p<0.001$).

Figure 1C:
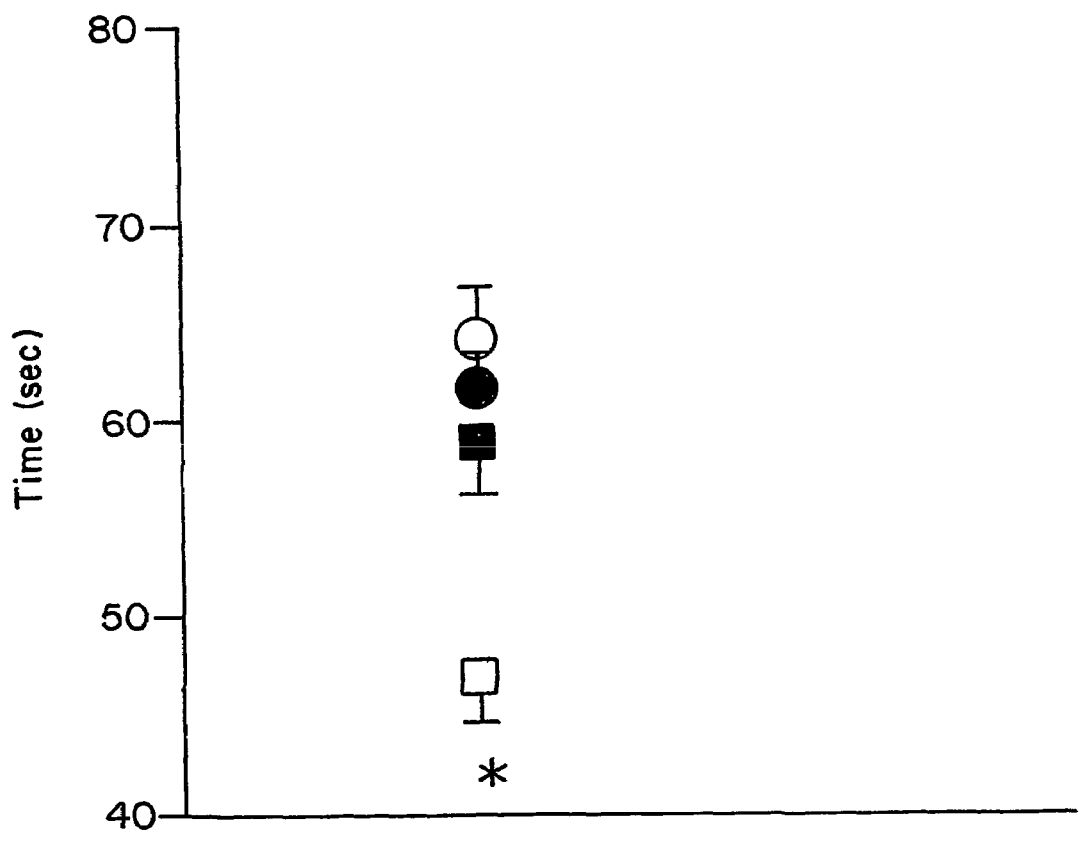

FIG. 1C depicts the results of the probe trial that assessed spatial memory. After 4 days of training and testing, the platform was removed and on day 5, the animals were subjected to swimming in a pool without the platform. It was apparent from the probe trial that the time spent in the quadrant of the pool where the platform was previously positioned was significantly increased ($p<0.001$) in the AF64A-treated animals that were given ADNF-9.

Figure 2A:
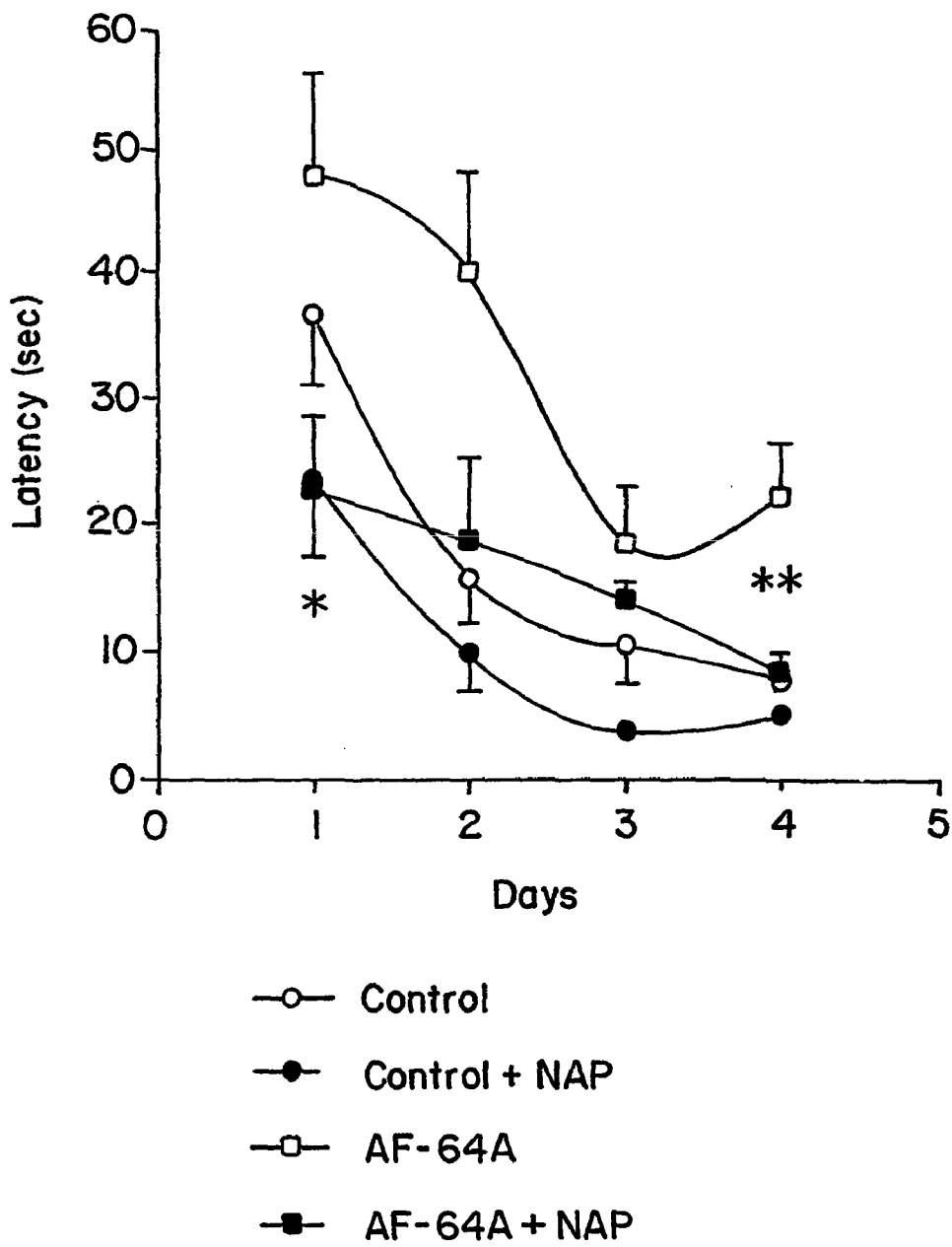
FIG. 2 AF64A-treated rats exhibit impairments in learning and memory that are ameliorated by intranasal administration of NAP. The same experiment reported in FIG. 1 (A, B, C, respectively) was repeated, except that the peptide used was NAP and the number of animals per each of the experimental groups was 10-20 and 27 for the AF64A-treated group.
Figure 2B:
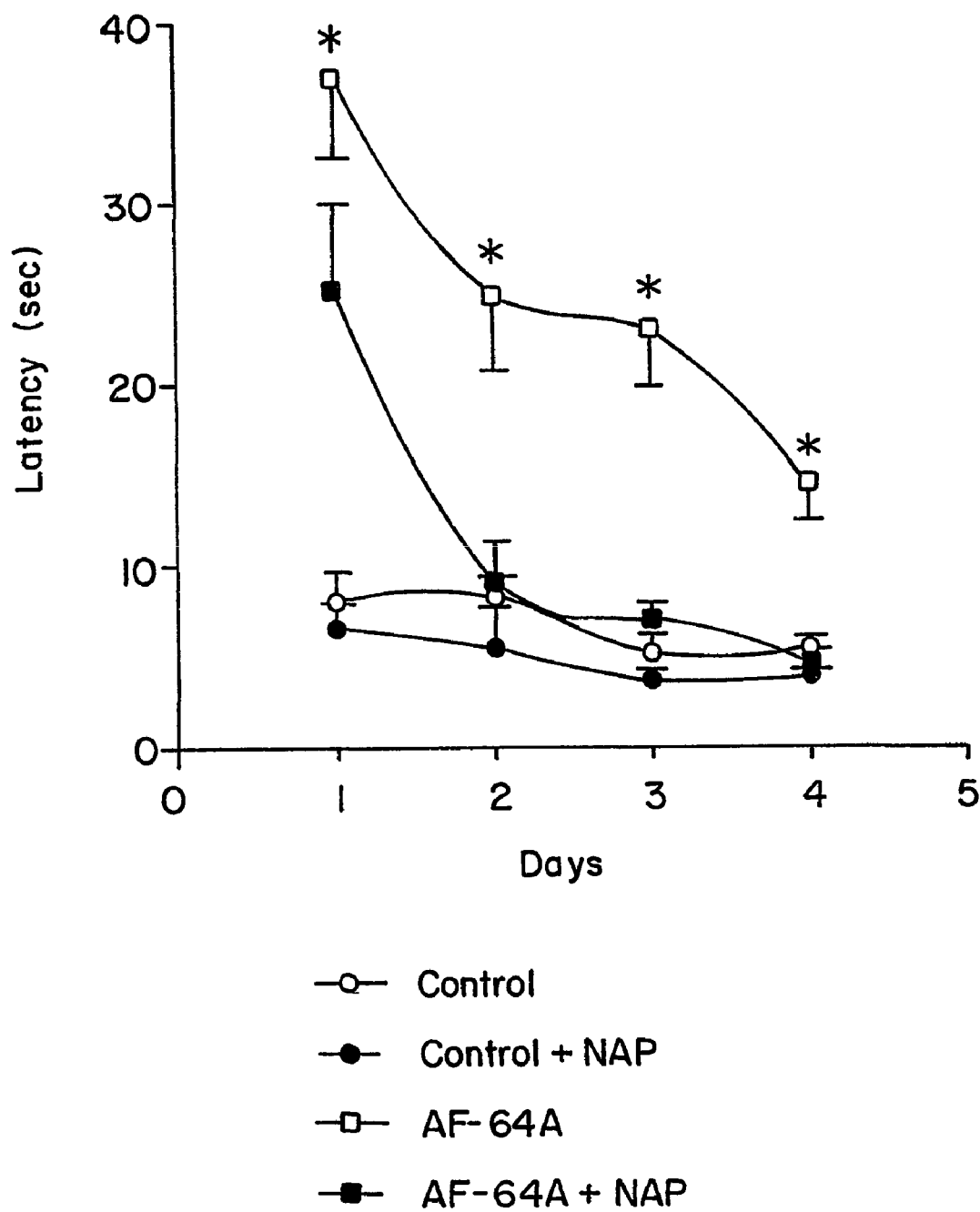
Figure 2C:
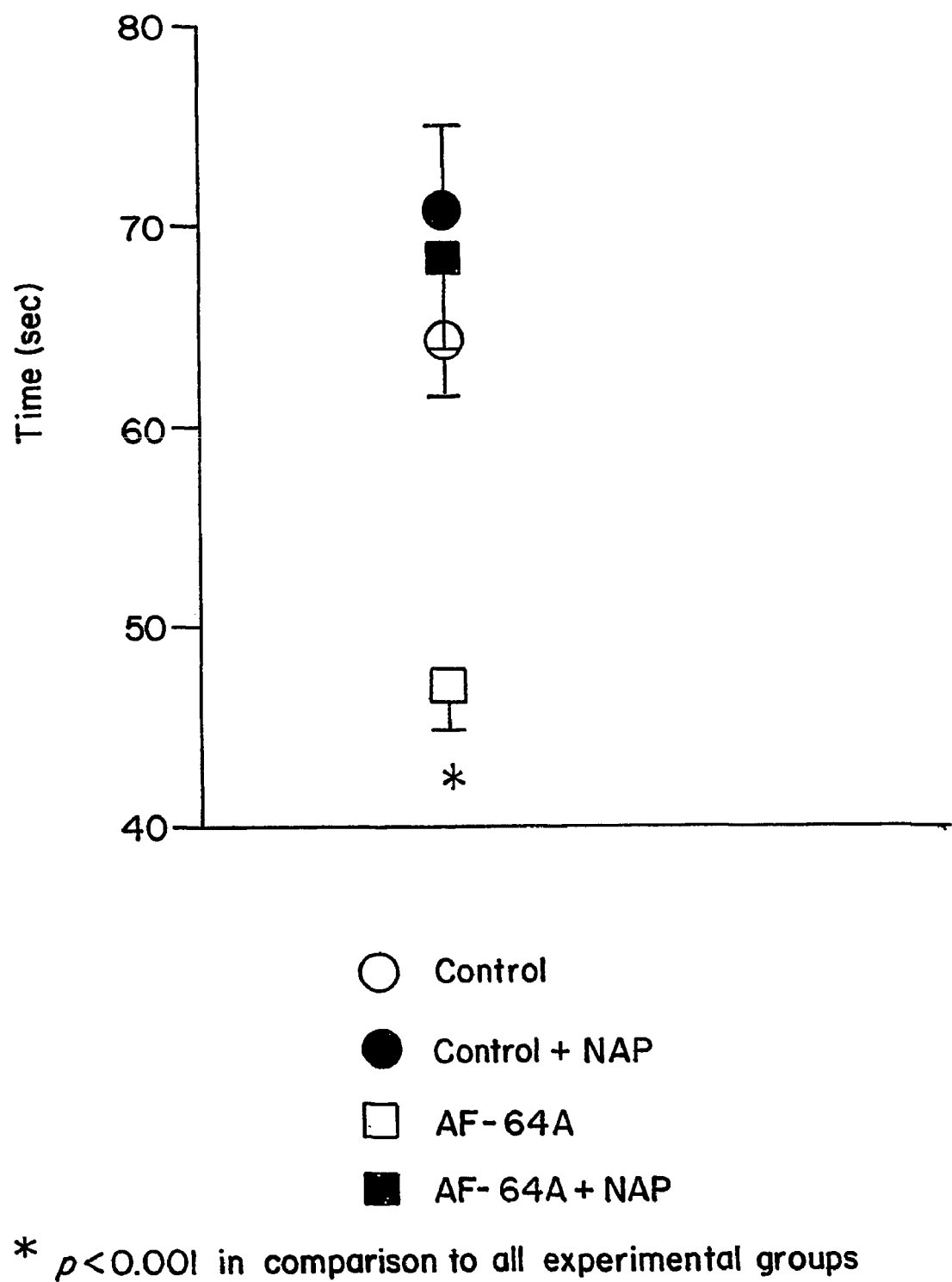

Intranasal Administration of NAP Protects Against Short-Term Memory Loss Associated with AF64A-Treatment In Vivo An experiment similar to the one described for ADNF-9 was performed with NAP in control animals and AF64A-treated animals. Here too, the peptide was administered by intranasal application. On day one, in the first daily test, immediately after placement on the hidden platform (testing reference memory), NAP-treated animals were significantly improved as compared to vehicle-treated controls (FIG. 2A, $p<0.001$). As was indicated above AF64A treatment resulted in reduced performance in the water maze paradigm and here, NAP-treated AF64A-impaired animals were significantly different from vehicle-treated AF64A-impaired animals on the fourth day of testing (FIG. 2A, $p<0.041$). In the second daily test, indicative of short-term memory, NAP-treated AF64A-impaired animals were improved throughout the experiment and reached control levels already on testing day 2 (FIG. 2B, $p<0.001$). After 4 days of training and testing, the platform was removed and on day 5, the animals were subjected to swimming in a pool without the platform (as above). Results showed that the time spent in the quadrant of the pool where the platform was previously positioned was significantly increased (FIG. 2C, $p<0.001$) in the AF64A-treated animals that were given NAP as compared to AF64A-vehicle-treated animals. Furthermore, peptide-treated groups (control-sham-lesion, or AF64A-lesion) were not significantly different from control (sham-lesion) animals and an apparent insignificant improvement was noted in the NAP-treated groups in comparison to control (sham-lesion) animals (FIG. 2C).

Intranasal Administration of NAP Protects Memory in Control Animals In Vivo

An experiment similar to the one described was performed with NAP in control animals. Here too, the peptide was administered by intranasal application. As shown in FIG. 2A, in the first daily test, immediately after placement on the hidden platform (testing reference memory), NAP-treated control animals were significantly improved as compared to control animals not treated with NAP (FIG. 2A).

Bioavailability and Stability of NAP

In the above water maze tests, NAP administration resulted in an apparently enhanced behavioral improvement as compared to ADNF-9 application (FIG. 1 vs. FIG. 2). Previously, ADNF-9 was less effective than NAP in ameliorating memory deficits in the apolipoprotein E-deficient mice (Bassan et al., *J. Neurochem.* 72:1283-1293 (1999)) and PBS solutions of ADNF-9 lost biological activity upon storage at temperatures $<4°$ C. (Brenneman et al., *J. Pharmacol. Exp. Therap.* 285:619-627 (1998)). It was thus decided to evaluate the bioavailability and stability of NAP as a future therapeutic.

Figure 3A:
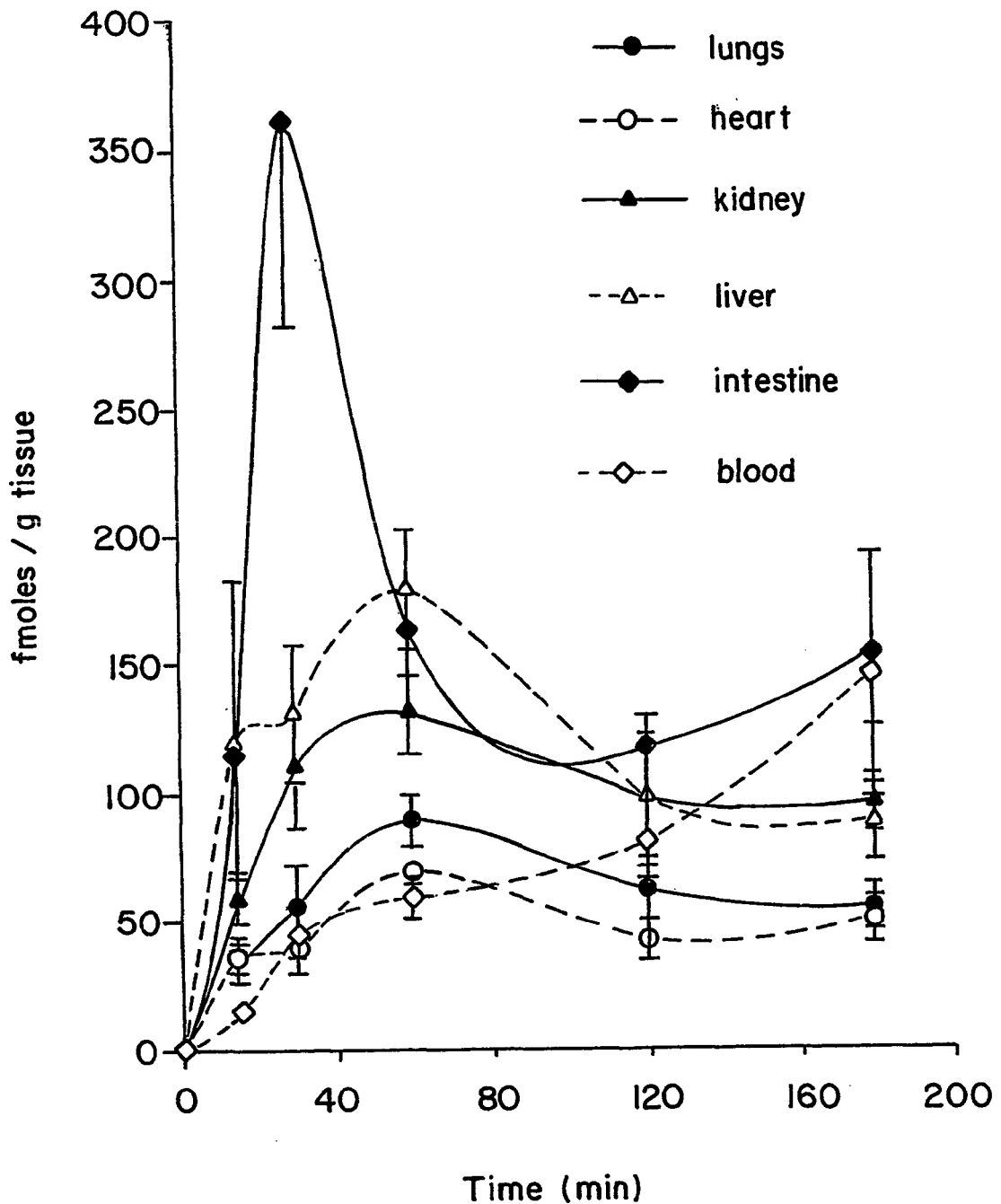
FIG. 3 Intranasally applied [$^3$H]-NAP reaches the body and the brain. (A) Animals were sacrificed at indicated times after administration and tissue samples were weighed and assayed (in duplicates) for radioactivity in a β-counter, a mean of four animals is depicted. (B) Brains were dissected at indicated time points and radioactivity monitored. (C, D) Intact [$^3$H]-NAP reached the brain after intranasal administration. Radioactive tissue samples (cerebral cortex) were homogenized and subjected to low-speed centrifugation. Supernatants (30 minutes following application, closed circles, C, and 60 minutes following application, closed triangles, D) were analyzed by HPLC fractionation against [$^3$H]-NAP stock (open circles). Samples were monitored for radioactivity (dpm) in a β-counter. All results were calculated to depict radioactivity as fmoles of NAP/g tissue. (E) The experiment was repeated with three additional animals, here the animals were 200 g each instead of 250-300 g in A-D and small visible blood vessels were removed utilizing watchmaker's forceps (no. 5).
Figure 3B:
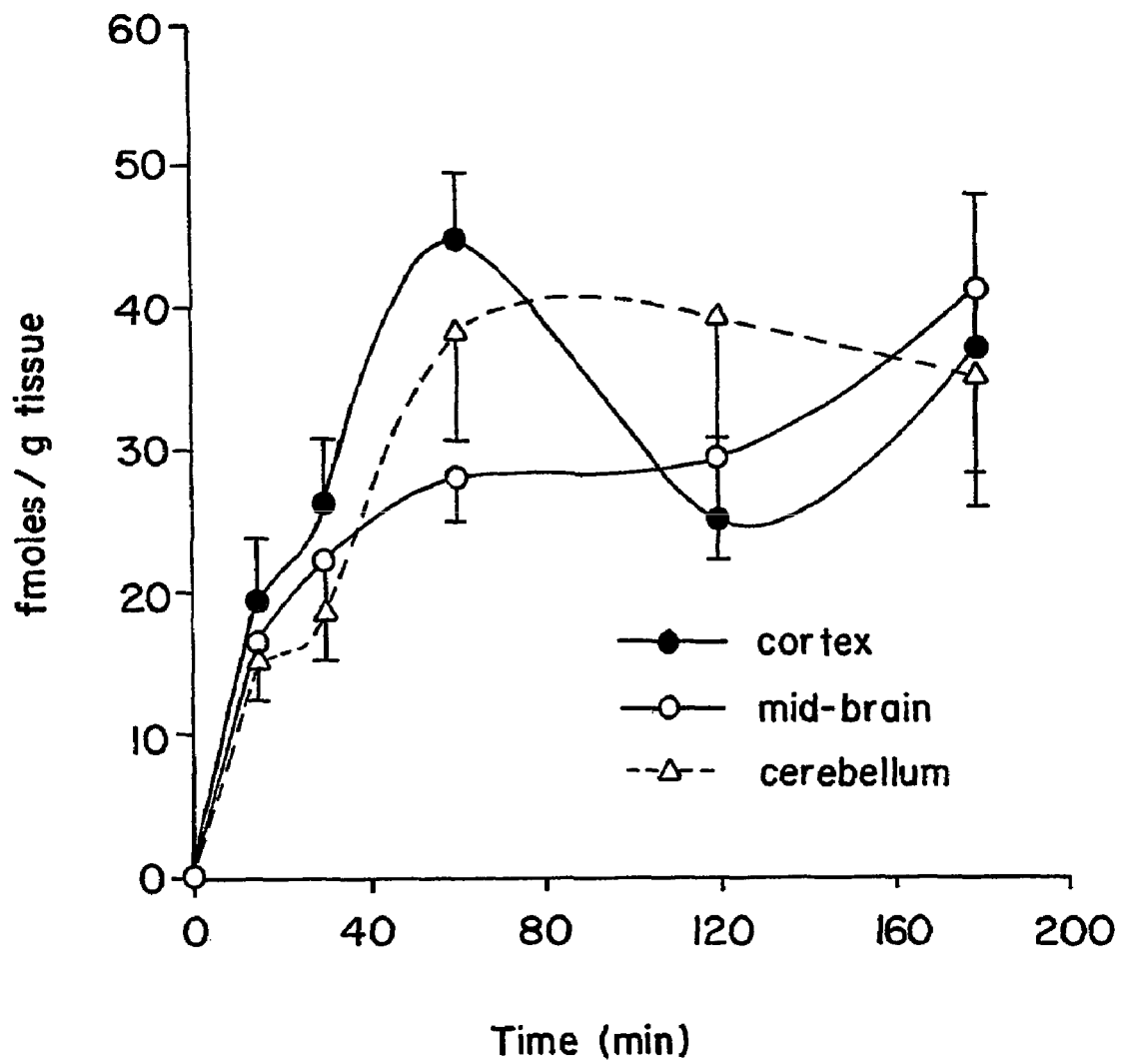
Figure 3C:
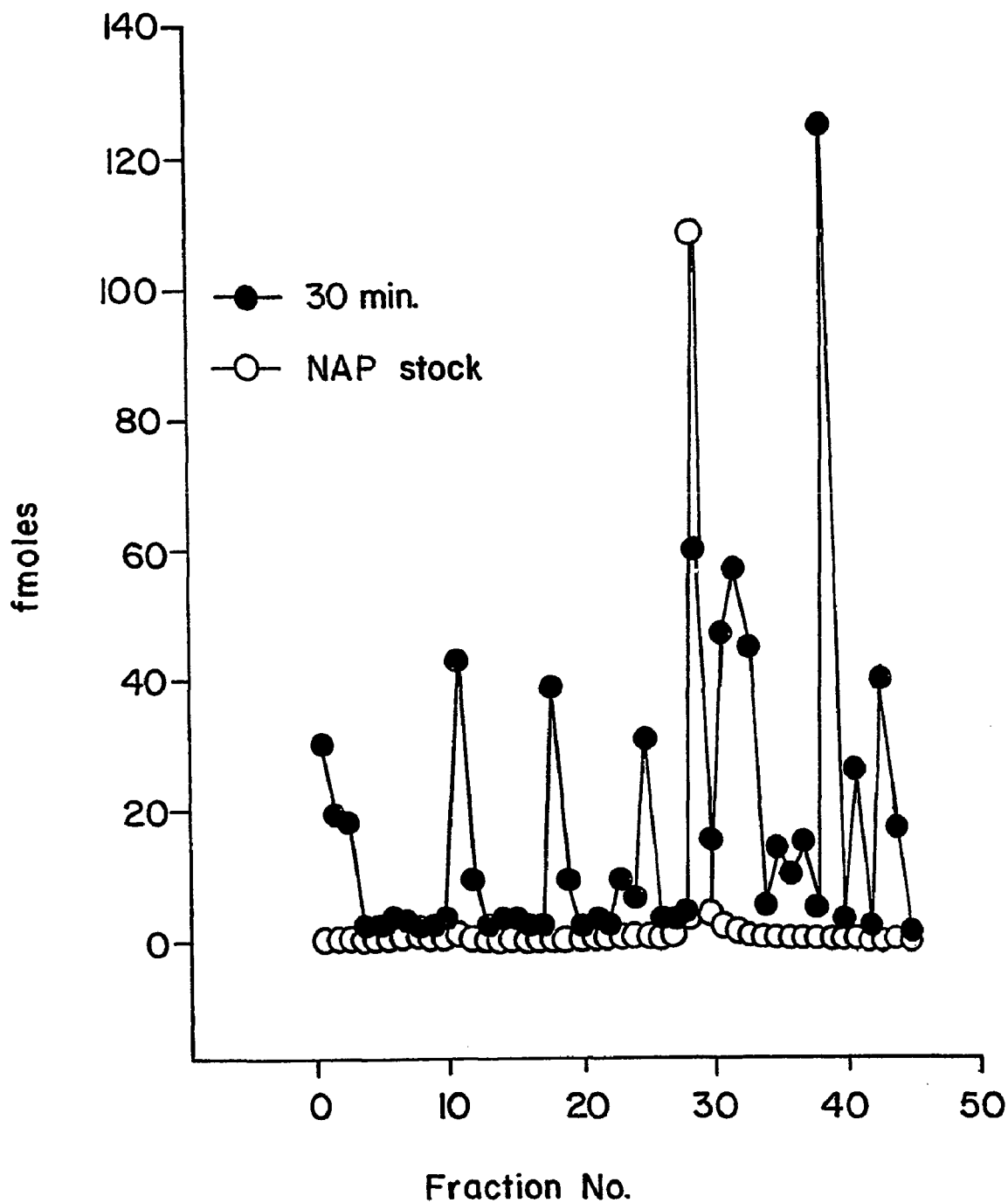
Figure 3D:
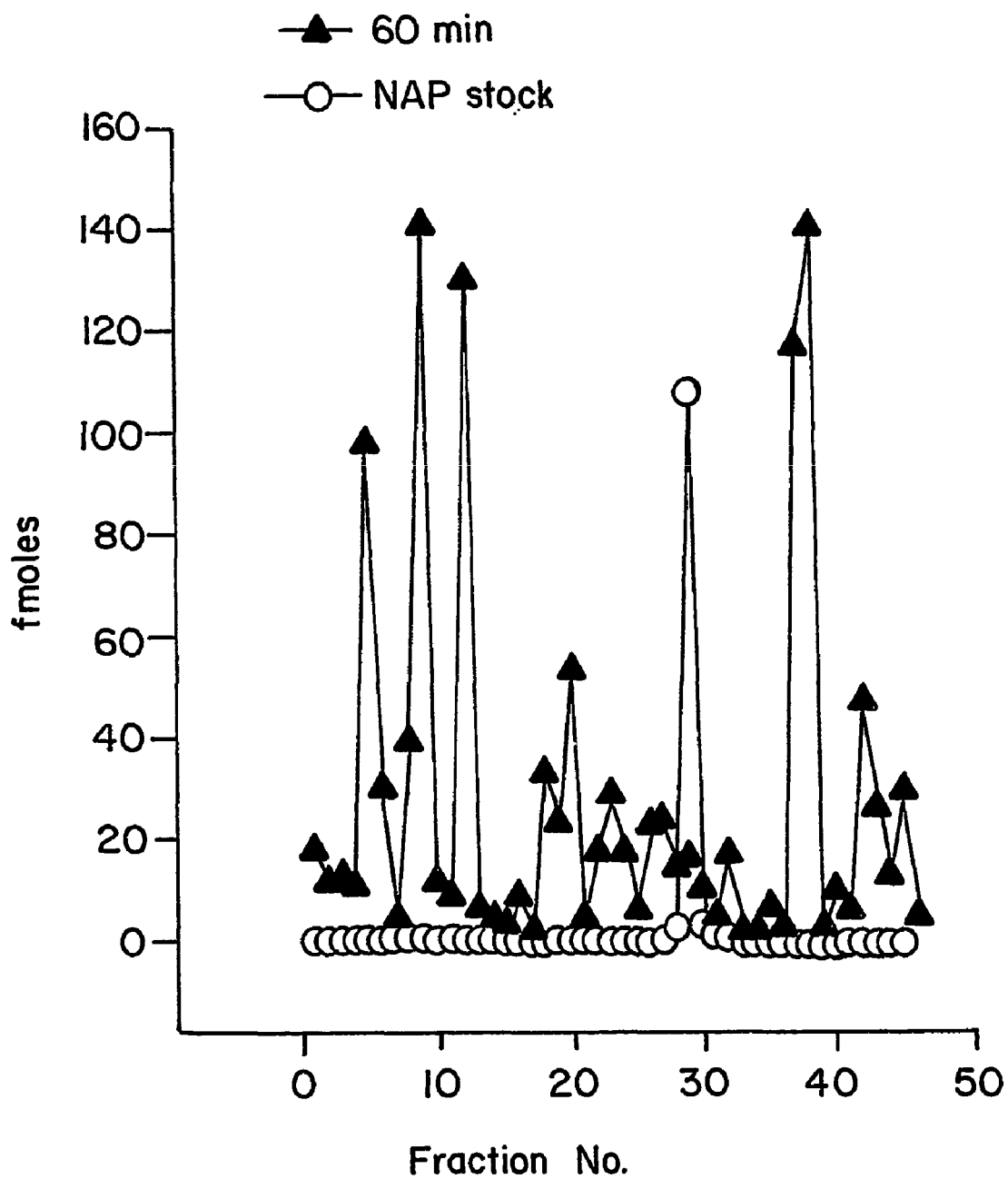

A time course of distribution of [$^3$H]-NAP that was applied intranasally was measured in the various organs of the body. Results (FIG. 3A) demonstrated high levels of total radioactivity (calculated as fmoles NAP/g tissue) in the intestine and liver, with highest levels in the intestine, thirty minutes after administration. The total radioactivity in the brain (cortex) was highest 60 minutes following administration (FIG. 3B). Each animal received five microliter of [$^3$H]-NAP containing 2.5 million dpm (22.75 pmole). If distributed homogeneously in the 250 g rat then 91 fmoles/g tissue are assumed (with 300 g rats having 75.5 fmoles/g tissue). These results indicated 45 fmoles/g tissue. Reversed-phase high performance liquid chromatography (RP-HPLC) suggested that the peptide was intact in the brain 30 minutes following application (FIG. 3C). Of the 807.8 fmole/g tissue eluted from the column, 98 fmoles/g tissue co-migrated with intact NAP suggesting that at least 12% of the material was intact, in the brain, 30 mm. following application. Sixty minutes following application, of the 1198.9 fmoles/g tissue eluted from the column only 2% co-eluted with intact radioactive NAP (FIG. 3D).

These results suggested that the half-life of NAP in the cortex is about 15 minutes. Close examination of FIGS. 3A and 3B showed higher levels of the radioactive NAP in the blood than in the cortex especially three hours following administration, a time when the peptide is probably completely broken down (FIG. 3D). Thus, the increased level of radioactivity in the blood, at later times following peptide application may reflect peptide breakdown and dissipation.

Figure 3E:
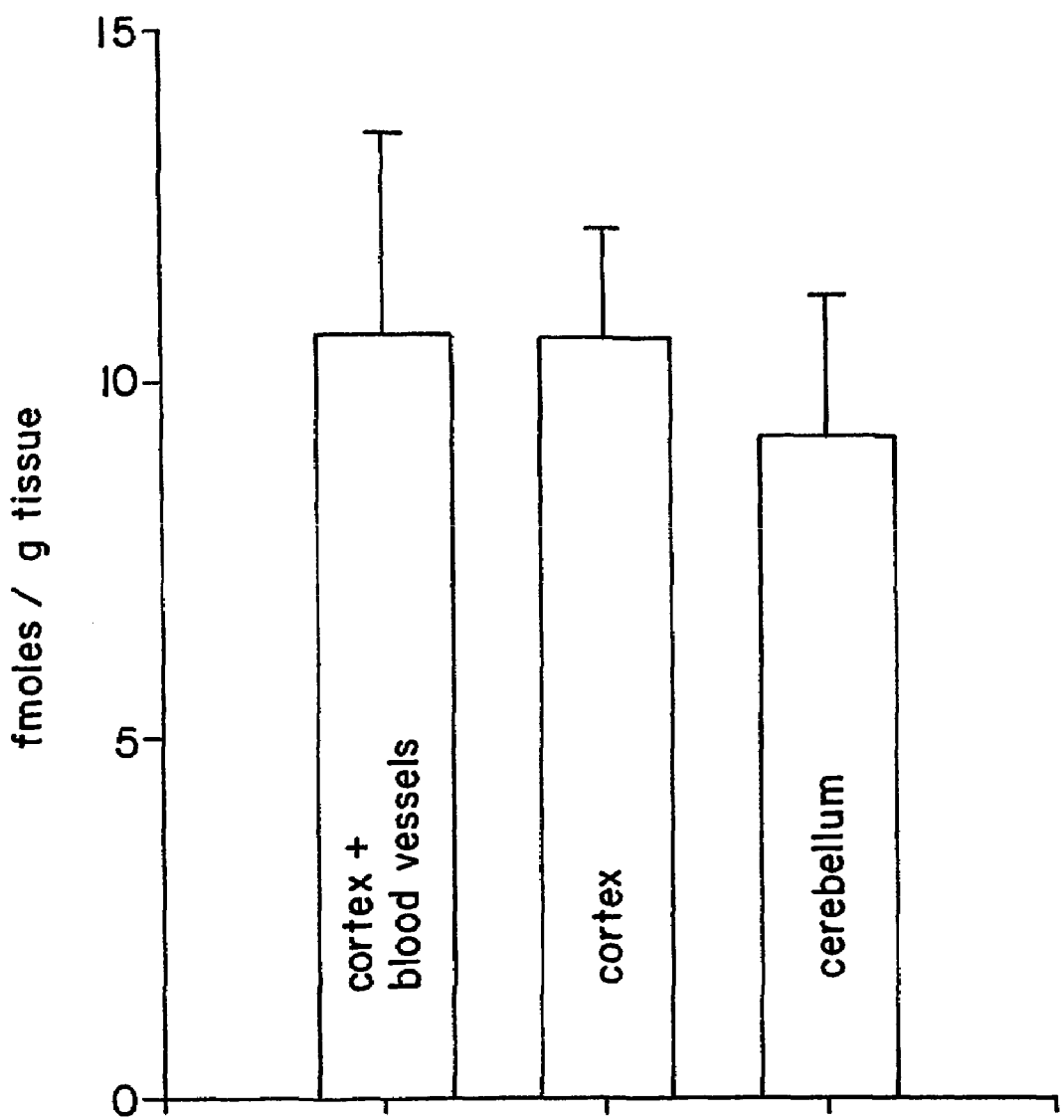

To examine the question whether the peptide is present in brain tissue, rather than within cerebral blood vessels, an additional experiment was performed. Here, 200 g male rats were treated as above and thirty minutes following peptide application (a time when the peptide is still intact, FIG. 3C) brains were dissected and small visible blood vessels were carefully removed. Results demonstrated that although some of the radioactivity was due to small visible blood vessels, most of it was found in the apparent brain tissue, with visible blood vessels contribution being insignificant (FIG. 3E). Furthermore, the cerebellum (free of small visible blood vessels) which is further away from the olfactory bulb than the cortex, had apparently less radioactive peptide accumulation. However, the difference between the cerebral cortex and the cerebellum was not significant, suggesting rapid peptide distribution (FIGS. 3B and 3E).

Figure 4A:
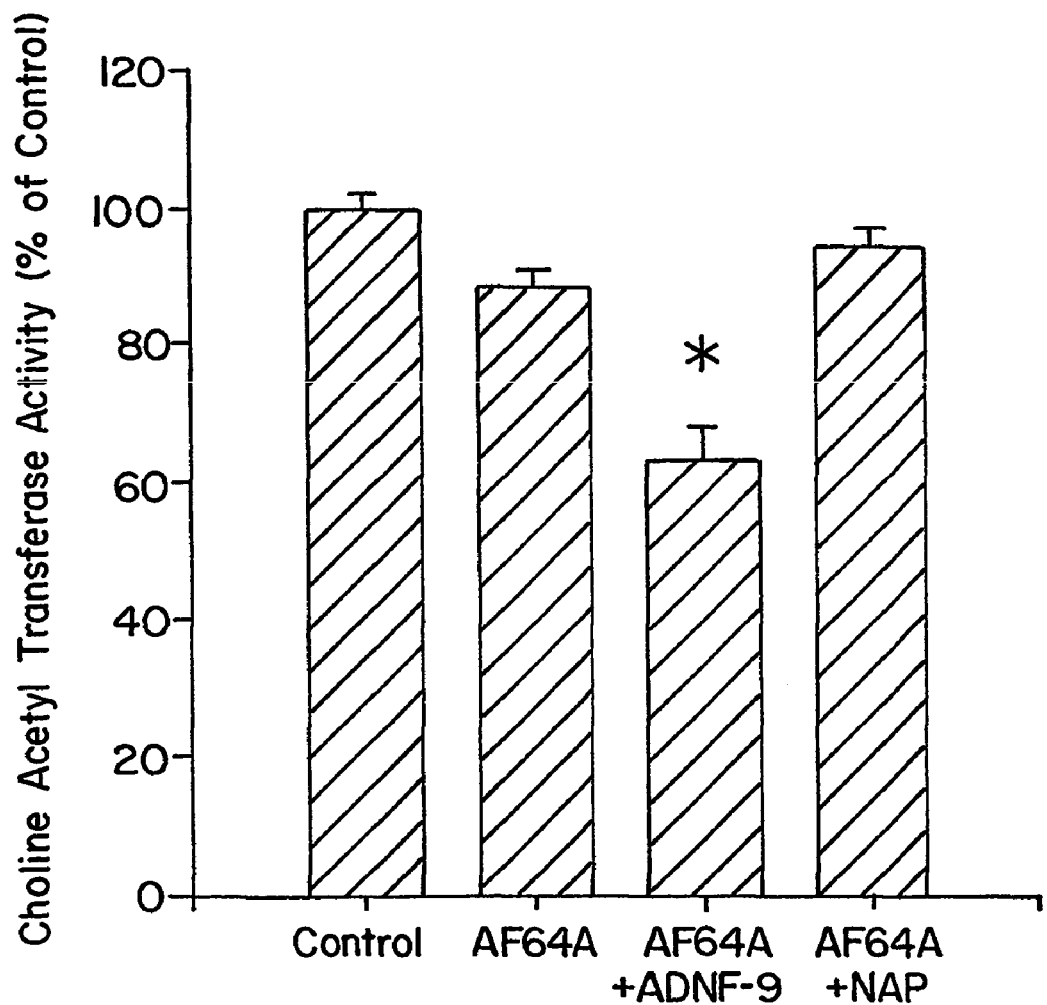
FIG. 4(A) Intranasal application of NAP prevents reduction in choline acetyl transferase activity in AF64A-treated rats. Incorporation of radiolabeled choline into acetyl choline is shown. Results were calibrated against control (100%). Experiments utilizing three animals per group (each in triplicates) were conducted and analyzed as described in the text. (3) AF64A-treated rats exhibit impairments in learning and memory, long-lasting effects of NAP, but not of ADNF-9 treatment. Ten male rats (as described in the methods section) were used per experimental group. Four groups were used, three were treated with AF64A and one group was treated with saline (control). The rats were allowed a week for recovery, and then two AF64A groups were treated (intranasally) with either ADNF-9 or NAP. Following 5 treatment days the animals were allowed to recover for two days and then subjected to daily water-maze tests (as in FIGS. 1 and 2). The difference between this experiment and the experiments in FIGS. 1 and 2 is that the animals did not receive a daily intranasal application of peptides prior to the behavioral test. The figure depicts the second daily test indicative of short-term memory.

AF64A-Treated Animals Exhibit a Reduction in Choline Acetyl Transferase Activity, Protection by NAP Enzymatic assays on brain extracts derived from AF64A-treated animals and sham-treated controls (three animals per group, each in triplicates) revealed a very minor reduction (11+2.6%) in choline acetyl transferase activity at the termination of the experiment (FIG. 4A). NAP treatment of AF64A-animals resulted in increased cholinergic activity indistinguishable from control (sham operated) values (FIG. 4A, 100% choline acetyl transferase activity indicated 130 pmol/mg protein/minute).

In four groups of animals, three were treated with AF64A, allowed a week for recovery, and then two groups were treated (intranasally) with either ADNF-9 or NAP. Following 5 treatment days the animals were allowed to recover for two days and then subjected to daily water-maze tests (as in FIGS. 1 and 2). The difference between this experiment and the experiments described above (FIGS. 1 and 2) is that the animals did not receive a daily intranasal application of peptides prior to the behavioral test. NAP treated AF64A-animals were not significantly different from control rats and were significantly faster in finding the hidden platform in the water maze as compared to the ADNF-9-treated AF64A-rats (p<0.022).

Discussion

The present study has demonstrated in vivo efficacy for ADNF neuroprotection. Intranasal administration of ADNF-9 or NAP protected against loss of short-term memory associated with AF64A-treatment. NAP administration also improved reference memory in control animals. Furthermore, NAP protected against reductions in choline acetyl transeferase activity, as was demonstrated before also for apolipoprotein E deficient mice (Bassan et al., *J. Neurochem.* 72:1283-1293 (1999)). NAP distribution in the brain and the body was rapid. The calculated half-life of NAP in the brain following intranasal administration was about 15 minutes. HPLC analysis indicated that NAP is metabolized in vivo to multiple fragments, suggesting the possibility of active metabolites.

Figure 4B:
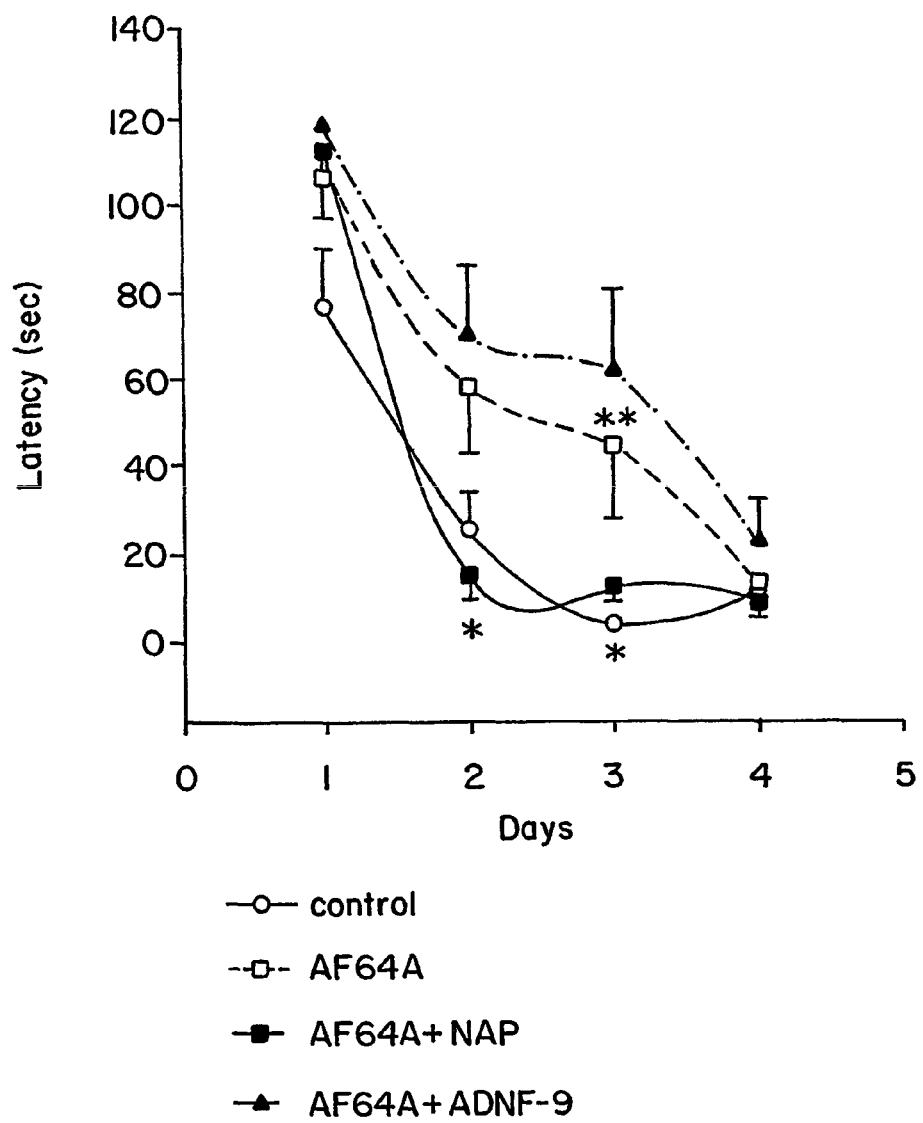

The effects of ADNF-9 and NAP on cholinergic activity (FIG. 4A) and in the behavioral tests (FIG. 4B) suggest the possibility that the two peptides act through different mechanisms to improve cognitive functions, with ADNF-9 having an immediate short-term effect. Furthermore, animals treated with NAP by intranasal application exhibited increased learning and memory abilities in the water maze test as compared to ADNF-9-treated animals (FIGS. 1 and 2). Similarly, injection of NAP (and not of ADNF-9) to newborn apolipoprotein E-deficient mice prevented short-term memory deficits in the three-week-old pups (Bassan et al., *J. Neurochem.* 72:1283-1293 (1999)).

These studies suggest a wide range of neuroprotective activities for NAP. Indeed, NAP (over a wide range of concentration) provided protection against buthionine sulfoximine induced decreases (70-90%) in neuroblastoma cell viability (Offen et al., *Brain Research* 854:257-262 (2000)). Buthionine sulfoximine, a selective inhibitor of glutathione synthesis, causes a marked decline in reduced glutathione in neuronal cell models leading to decreased viability (Offen et al., *Brain Research* 854:257-262 (2000)). Thus, the mechanism of neuroprotection by NAP may be mediated through raising cellular resistance against oxidative stress, a general mechanism affecting cell survival. Furthermore, preliminary toxicology studies have shown no toxic effects for this peptide.

In conclusion, the demonstrated in vivo efficacy of NAP coupled with its bioavailability and apparent stability identify it as an attractive lead compound for the development of therapeutic agents against neurodegenerative diseases. Currently available drugs for symptomatic treatment of Alzheimer's disease target directly the function of the cholinergic system. An example is tacrine, an inhibitor of acetyl chlorine esterase (van Reekum et al., *Can. J. Psychiatry* 42 suppi.1: 35S-50S (1997)). However, growth factors treatment may afford a broader range of neuroprotection, hence studies on in vivo effects of neurotrophic factors provide important basic information and open new horizons for drug design.

Example II

Prenatal Administration of ADNF Polypeptides Provides Postnatal Enhanced Learning and/or Memory Materials and Methods Animals and Treatment C57-B16J female mice (Jackson Labs) were kept under a 12 h light, 12 h dark regimen with food and water available at all times. The mice received humane animal care in compliance with the "Guideline for Care and Use of Experimental Animals." Six week old females (21-24 grams) were mated with C57-B16J males for 4 h. The presence of a vaginal plug was considered day 0 pregnancy.

Animals were injected intraperitoneally on pregnancy day 8, or treated on pregnancy day 8 after 1 hour fast with gavage dose of ADNF polypeptides. NAP was diluted in 50 µl DMSO and diluted in filtered Dulbecco's phosphate buffered saline (DPBS). SAL was dissolved and diluted in filtered DPBS. Control animals were treated with a vehicle (i.e., DPBS). All treatments were coded.

Delivery occurred on day 20, weaning on day 20 of life. Male offspring were eartagged with all identifying markers of coded treatments removed.

Morris Water Maze Test

Only male mice were used for the water maze trials. Testing of mice began at 35-50 days, typically on day 38, twice daily (two trials) for 7 days.

Morris water maze test used is adapted from "repeated acquisition of a spatial navigation task in mice: Effects of spacing of trials and of unilateral middle cerebral artery occlusion" Klapdor & Van der Staay, *Physiology & Behav.* 63(5):903-909 (1998). A trial consists of attempting to find the hidden platform from 4 set points. Specifically, testing of mice began in the mornings, typically between 9 and 9:30. Consistent timing is important to any behavioral study. Testing of mice was performed in a random order to prevent chronological bias by the researcher. Maze was set up the day before, to allow water time to adjust to room temperature. 100-150 ml of non-toxic white tempura is added and mixed. Before beginning each day, water is agitated to homogenize paint, and additional water is added to assure that a consistent water level of 7-10 ml above the platform is maintained despite evaporation. The software is set up so that the masking is optimal, and each of two trials is timed at 60 seconds. The active platform is set for the number 1 quadrant.

Mice are allowed to sit on the platform for 1 minute on Day 1, in order to acclimate to their surroundings and gain an initial sense of where the escape platform is located. It is normal for the mice to jump off the platform and swim around in exploration at this initial stage. This should be permitted briefly, but the mice should be returned to the platform after a few seconds of swimming is completed.

Mice are released into the maze from the midline separating quadrants 2 and 3 (west), facing the outside of the maze. They are allowed to swim for 60 seconds, or until they reach the platform on their own. If they are unsuccessful in finding the platform, they are manually returned to it. All mice are allowed to remain on the platform for 15 seconds after their first trial.

The second trial is then administered in the same manner as the first (same release position, same platform position, etc.), again allowing the mice 15 seconds on the platform before returning them to their drying cages (equipped with chix wipe to absorb extra water).

On days 2-7, mice are only given 15 seconds on the platform before the initial trial. This is enough for them to become adjusted to the water temperature. Their propensity to flee the platform during this stage exhibits a remarkable declination from day one, as most mice will stay without attempting to leave the platform. The daily average escape latency is calculated and plotted along the 7 day period for test administration. Many mice exhibiting decreased spatial learning and memory will display behavioral anomalies, including thigmotaxis (wall hugging) and floating. This has been documented by Minichiello et al., Neuron 24(2):401-414 (1999).

The average of the two trials was taken and used for statistical analysis. Statistical analysis was with ANOVA with Bonferroni correction for multiple analyses (overall P<0.007 considered significant) and Fisher's post hoc for determination of significantly different pairs.

Statistics

Statistical analysis included ANOVA for continuous variables, Mann-Whitney U for nonparametic data, Chi square for categorical variables or Fisher's exact test where appropriate (Statview 4.5 (Abacus Concepts, Inc., Berkeley, Calif.)) with p<0.05 considered significant. Results are presented as mean±standard error unless specified.

Results

Effects of Prenatal L-NAP+L-SAL Treatment

Pregnant mothers on pregnancy day 8 were treated with intraperitoneal injection of L-NAP (NAPVSIPQ; SEQ ID NO:2, from ADNF III) (0.2 ml; 20 µg) and L-SAL (SALLRSIPA; SEQ ID NO:1, from ADNF I) (0.2 ml, 20 µg) (n=8) or vehicle alone (n=50).

Assessment of learning utilized the Morris water maze as described in the Materials and Methods Section. Starting on day 38, two trials per day were performed for 7 days in Morris water maze, one immediately following the other. Latency to find the hidden platform was recorded. All animals were tested in a random order daily. The average of the two trials was used for analysis.

Figure 5:
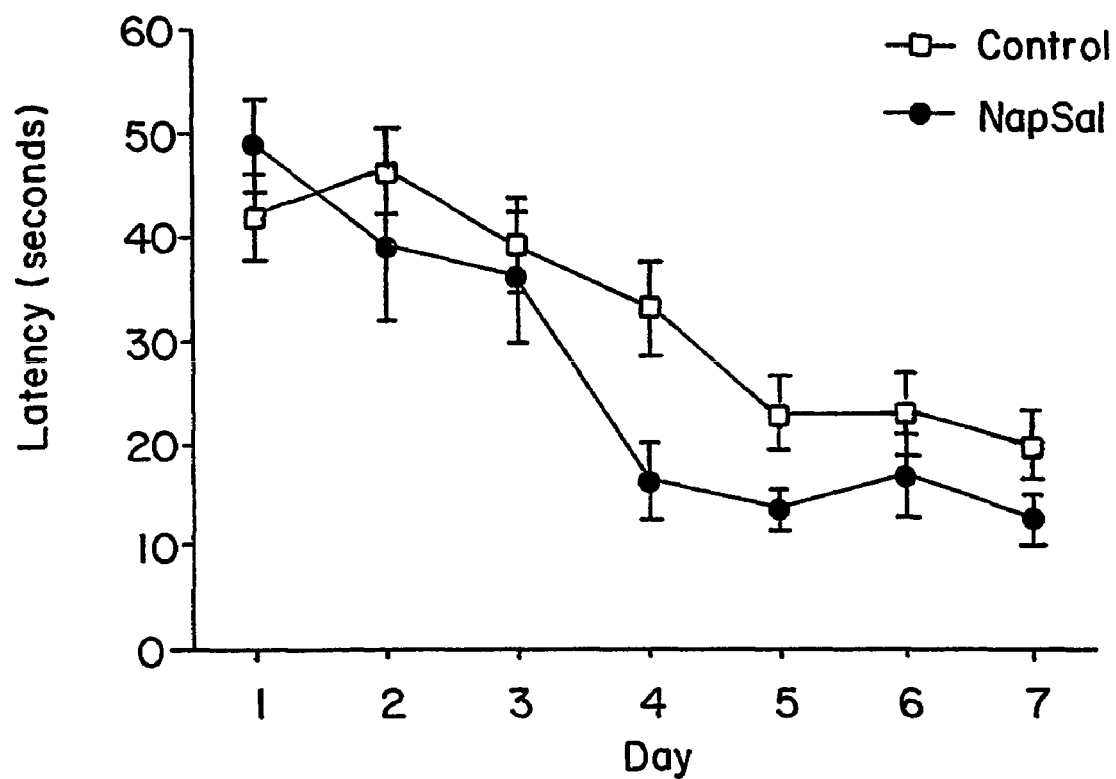
FIG. 5 illustrates the effects of prenatal treatment of animals with a mixture of L-NAP and L-SAL (intraperitoneal injection) on learning as assessed by a Morris water maze test.

As shown in FIG. 5, pups treated prenatally with L-NAP+L-SAL had an earlier onset of learning compared to the pups from control litters (P<0.03).

Effects of Oral D-NAP+D-SAL Administration

Figure 6:
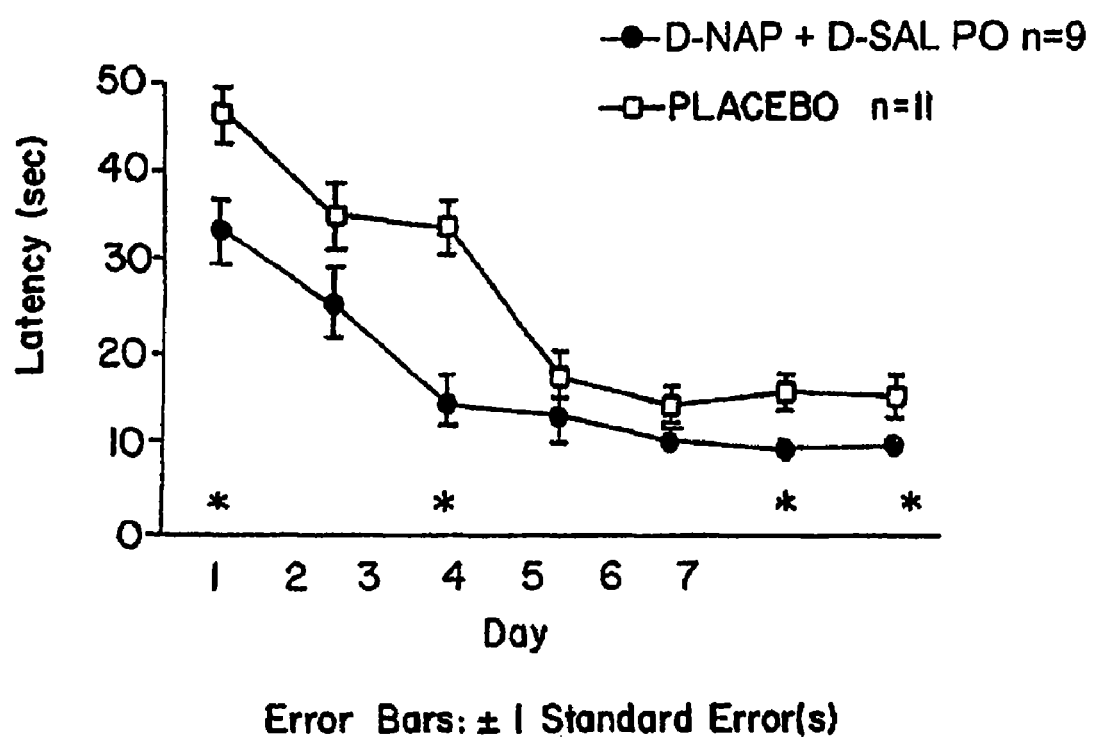
FIG. 6 illustrates the effects of prenatal treatment of animals with a mixture of D-NAP and D-SAL (oral administration) on learning as assessed by a Morris water maze test.

Pregnant mothers on pregnancy day 8, after 1 hour of fast, were treated with gavage dose (0.2 ml) of D-NAP (40 µg) and D-SAL (40 µg) (n=27) or vehicle alone (n=34). Assessment of learning utilized the Morris water maze as described in the Materials and Methods Section. Starting on day 38, two trials per day were performed for 7 days in Morris water maze, one immediately following the other. Latency to find the hidden platform was recorded. If the animal could not find the platform within 60 seconds, he was placed on the platform manually. All animals were tested in a random order daily. The average of the two trials was used for analysis. As shown in FIG. 6, animals who were exposed to oral D-NAP+D-SAL during pregnancy learned significantly faster than controls, with an earlier onset of learning and an overall decreased latency upon completion of the study.

Effects of Oral D-SAL Administration

Figure 7:
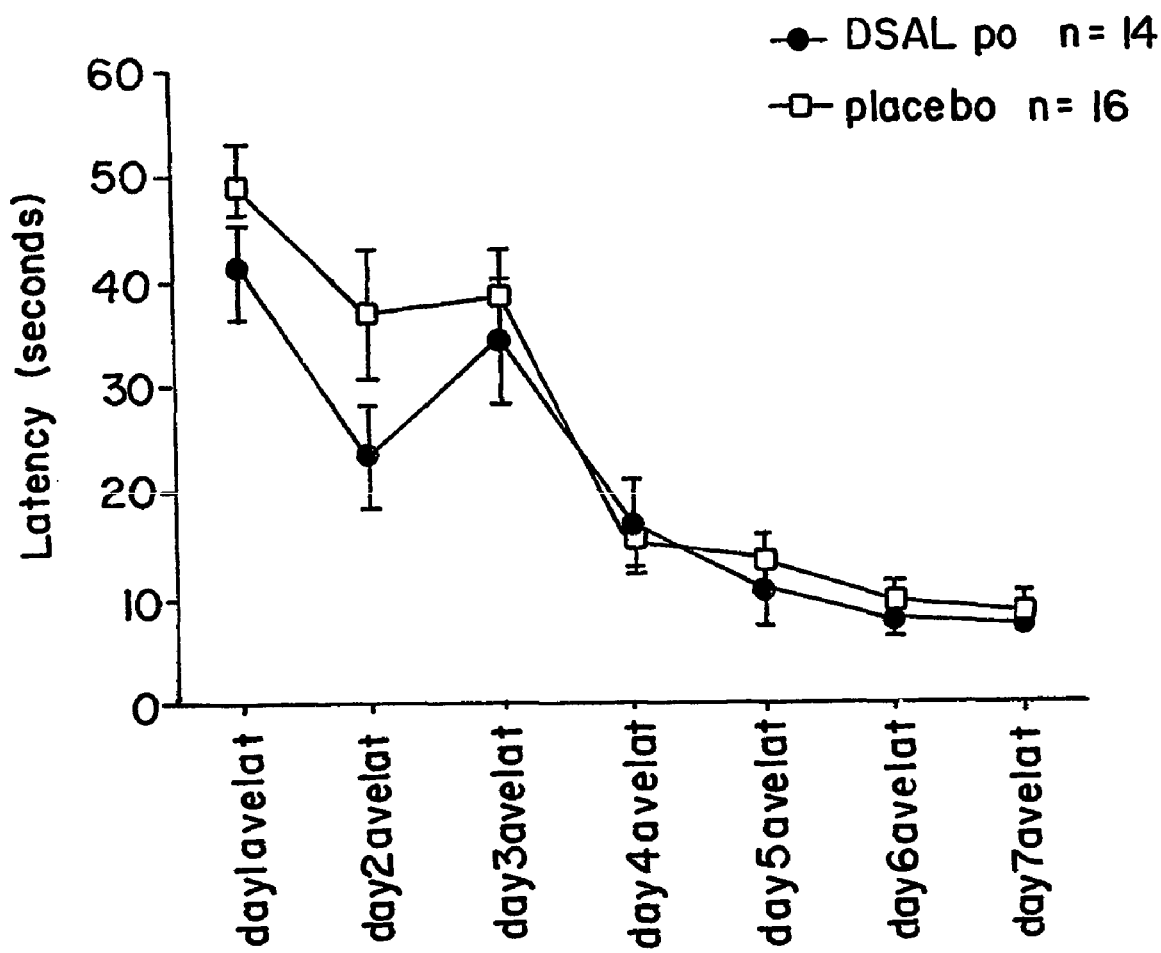
FIG. 7 illustrates the effects of prenatal treatment of animals with D-SAL (oral administration) on learning as assessed by a Morris water maze test.

Pregnant mothers on pregnancy day 8, after 1 hour of fast, were treated with gavage dose (0.2 ml) of D-SAL (40 µg) (n=14) or vehicle alone (n=16). Assessment of learning utilized the Morris water maze as described in the Materials and Methods Section. Two trials per day were performed for 7 days in Morris water maze, one immediately following the other. Latency to find the hidden platform was recorded. If the animal could not find the platform within 60 seconds, he was placed on the platform manually. All animals were tested in a random order daily. The average of the two trials was used for analysis. As shown in FIG. 7, animals who were exposed to oral D-SAL appeared to show a trend of faster latencies.

Effects of Oral D-NAP Administration

Figure 8:
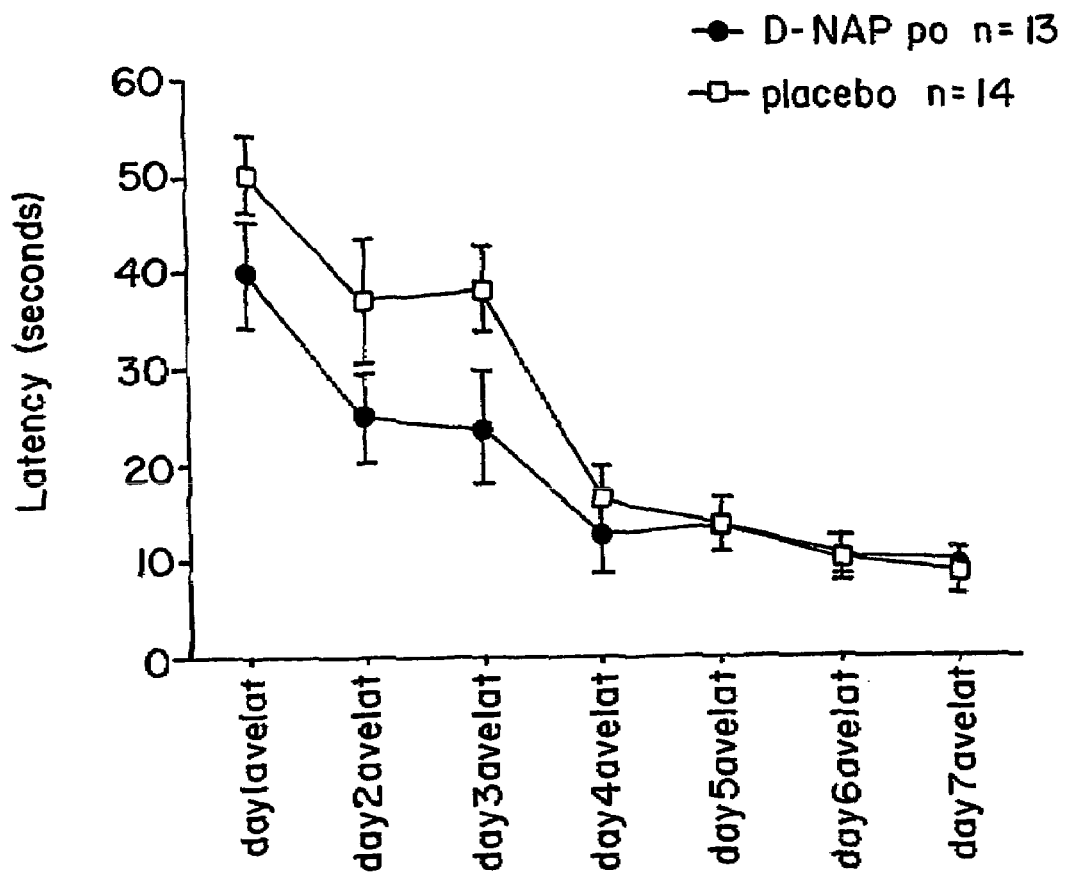
FIG. 8 illustrates the effects of prenatal treatment of animals with D-NAP (oral administration) on learning as assessed by a Morris water maze test.

Pregnant mothers on pregnancy day 8, after 1 hour of fast, were treated with gavage dose (0.2 ml) of D-NAP (40 µg) (n=13) or vehicle alone (n=14). Assessment of learning utilized the Morris water maze as described in the Materials and Methods Section. Two trials per day were performed for 7 days in Morris water maze, one immediately following the other. Latency to find the hidden platform was recorded. If the animal could not find the platform within 60 seconds, he was placed on the platform manually. All animals were tested in a random order daily. The average of the two trials was used for analysis. As shown in FIG. 8, animals who were exposed to oral D-NAP appeared to show a trend of faster latencies.

Effects of Oral D-SAL (Double Dose, 80 µg) Administration

Figure 9:
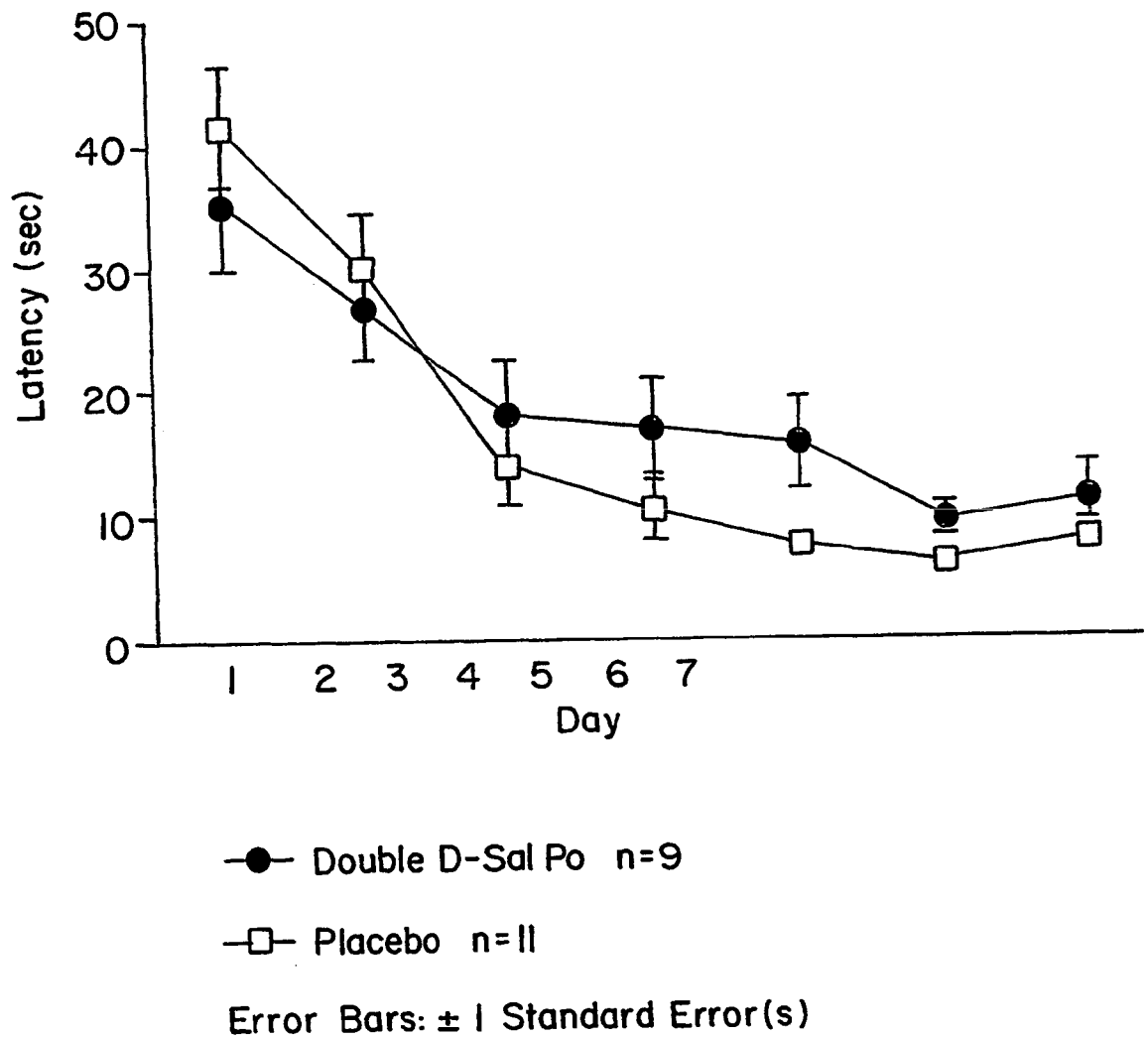
FIG. 9 illustrates the effects of prenatal treatment of animals with a double dose of D-SAL (oral administration) on learning as assessed by a Morris water maze test.

Pregnant mothers on pregnancy day 8, after 1 hour of fast, were treated with gavage dose (0.2 ml) of D-SAL (80 µg) (n=19) or vehicle alone (n=19). Assessment of learning utilized the Morris water maze as described in the Materials and Methods Section. Two trials per day were performed for 7 days in Morris water maze, one immediately following the other. Latency to find the hidden platform was recorded. If the animal could not find the platform within 60 seconds, he was placed on the platform manually. All animals were tested in a random order daily. The average of the two trials was used for analysis. As shown in FIG. 9, animals who were exposed to the double-dose of oral D-SAL appeared to perform similarly to the control animals.

Effects of D-NAP+D-SAL Administration on Probe Test

Figure 10:
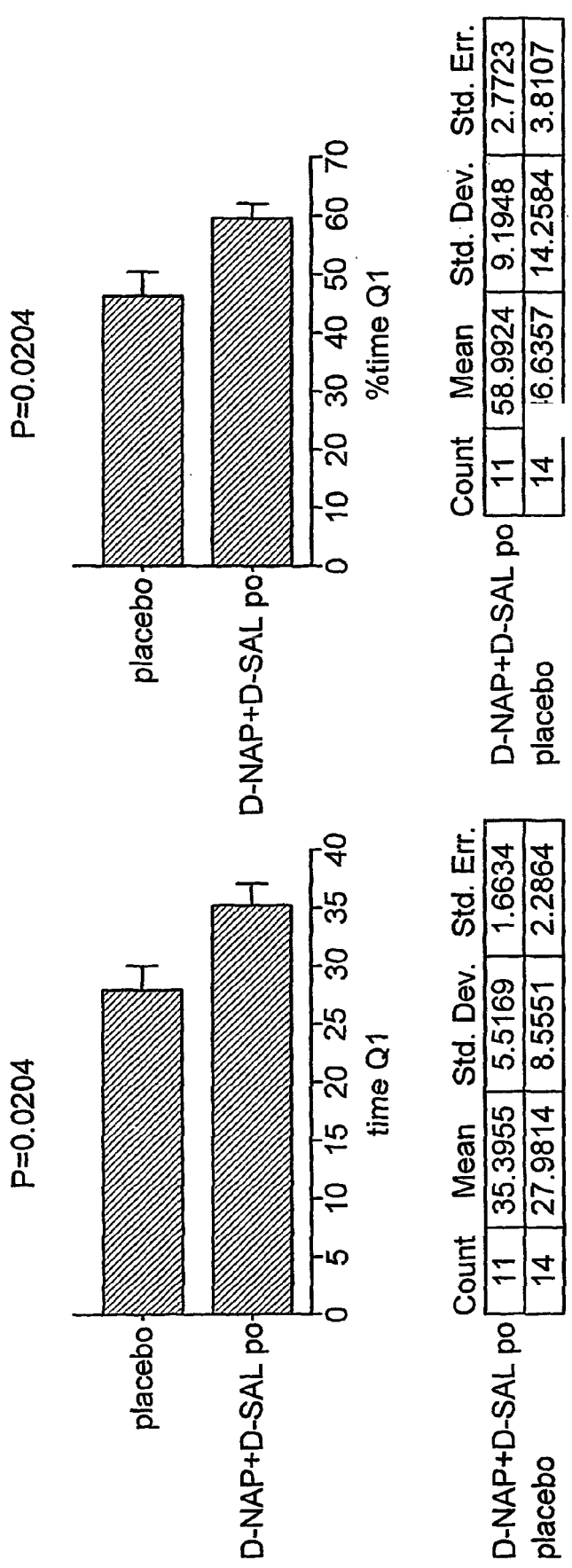
FIG. 10 illustrates the effects of prenatal treatment of animals with a mixture of D-NAP and D-SAL (oral administration) on learning as assessed by a probe test.

Pregnant mothers on pregnancy day 8, after 1 hour of fast, were treated with gavage dose (0.2 ml) of D-NAP (40 µg) and D-SAL (40 µg) (n=27) or vehicle alone (n=34). For those animals that were tested in the water maze test, learning in mice was further assessed using a probe test. In a probe test, the water maze test described above was modified by removing the platform. Th amount of time that animals spend in a quadrant, which used to have the platform, was measured. As shown in FIG. 10, animals who were exposed to D-NAP+D-SAL spent a significantly greater amount of time in the quadrant (which used to have the platform) compared to the control.

The present invention provides methods for improving performance (e.g., learning and/or memory) using ADNF polypeptides. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A method for improving learning and memory in a subject, the method comprising the step of administering postnatally to the subject in an amount sufficient to improve postnatal learning and memory of the subject, a mixture of:
   (a) an Activity Dependent Neurotrophic Factor (ADNF) I polypeptide comprising an active core site having the following amino acid sequence:
   Ser-Ala-Leu-Leu-Arg-Ser-Ile-Pro-Ala (SEQ ID NO:1); and
   (b) an Activity Dependent Neurotrophic Factor (ADNF) III polypeptide comprising an active core site having the following amino acid sequence:
   Asn-Ala-Pro-Val-Ser-Ile-Pro-Gln (SEQ ID NO:2); and
   assessing learning and memory of the post-natal subject, wherein the active core site of at least one of the ADNF I polypeptide and the ADNF III polypeptide comprises all D-amino acids.

2. The method of claim 1 wherein the active core site of the ADNF I polypeptide comprises all D-amino acids.

3. The method of claim 1, wherein the ADNF I polypeptide is Ser-Ala-Leu-Leu-Arg-Ser-Ile-Pro-Ala (SEQ ID NO:1).

4. The method of claim 1, wherein the ADNF I polypeptide is selected from the group consisting of:
   Val-Len-Gly-Gly-Gly-   Ser-Ala-Leu-Leu-Arg-Ser-Ile-Pro-Ala (SEQ ID NO:14);
   Val-Glu-Glu-Gly-Ile-Val-Leu-Gly-Gly-Gly-Ser-Ala-Leu-Leu-Arg-Ser-Ile-Pro-Ala (SEQ ID NO:15);
   Leu-Gly-Gly-Gly- Ser-Ala-Leu-Leu-Arg-Ser-Ile-Pro-Ala (SEQ ID NO:16);
   Gly-Gly-Gly-Ser-Ala-Leu-Leu-Arg-Ser-Ile-Pro-Ala (SEQ ID NO:17);
   Gly-Gly-Ser-Ala-Leu-Leu-Arg-Ser-Ile-Pro-Ala (SEQ ID NO:18);
   Gly- Ser-Ala-Leu-Leu-Arg-Ser-Ile-Pro-Ala (SEQ ID NO:19); and
   Ser-Ala-Leu-Leu-Arg-Ser-Ile-Pro-Ala (SEQ ID NO:1).

5. The method of claim 1, wherein the ADNF I polypeptide comprises up to about 20 amino acids at one or both of the N-terminus and the C-terminus of the active core site.

6. The method of claim 1, wherein the active core site of the ADNF III polypeptide comprises all D-amino acids.

7. The method of claim 1, wherein the ADNF III polypeptide is Asn-Ala-Pro-Val-Ser-Ile-Pro-Gln (SEQ ID NO:2).

8. The method of claim 1, wherein the ADNF III polypeptide is a member selected from the group consisting of:
   Gly-Gly-Asn-Ala-Pro-Val-Ser-Ile-Pro-Gln (SEQ ID NO:20);
   Leu-Gly-Gly-Asn-Ala-Pro-Val-Ser-Ile-PrO-Gln-Gln-Ser (SEQ ID NO:21);
   Leu-Gly-Leu-Gly-Gly-Asn-Ala-Pro-Val-Ser-Ile-Pro-Gln-Gln-Ser (SEQ ID NO:22);
   Ser-Val-Arg-Leu-Gly-Leu-Gly-Gly-Asn-Ala-Pro-Gln-Gln-Ser (SEQ ID NO:23); and
   Asn-Ala-Pro-Val-Ser-Ile-Pro-Gln (SEQ ID NO:2)

9. The method of claim 1, wherein the ADNF III polypeptide comprises up to about 20 amino acids at one or both of the N-terminus and the C-terminus of the active core site.

10. The method of claim 1, wherein the active core sites of both the ADNF I polypeptide and the ADNF III polypeptide comprise all D-amino acids.

11. The method of claim 1, wherein the ADNF I polypeptide is Ser-Ala-Leu-Leu-Arg-Ser-Ile-Pro-Ala (SEQ ID NO:1), and wherein the ADNF III polypeptide is Asn-Ala-Pro-Val-Ser-Ile-Pro-Gln (SEQ ID NO:2).

12. The method of claim 1, wherein the ADNF I polypeptide is a member selected from the group consisting of:
   Val-Leu-Gly-Gly-Gly-   Ser-Ala-Leu-Leu-Arg-Ser-Ile-Pro-Ala (SEQ ID NO:14);
   Val-Glu-Glu-Gly-Ile-Val-Leu-Gly-Gly-Gly-Ser-Ala-Leu-Leu-Arg-Ser-Ile-Pro-Ala (SEQ ID NO:15);
   Leu-Gly-Gly-Gly- Ser-Ala-Leu-Leu-Arg-Ser-Ile-Pro-Ala (SEQ ID NO:16);
   Gly-Gly-Gly-Ser-Ala-Leu-Leu-Arg-Ser-Ile-Pro-Ala (SEQ ID NO:17);
   Gly-Gly-Ser-Ala-Leu-Leu-Arg-Ser-Ile-Pro-Ala (SEQ ID NO:18);
   Gly- Ser-Ala-Leu-Leu-Arg-Ser-Ile-Pro-Ala (SEQ ID NO:19); and
   Ser-Ala-Leu-Leu-Arg-Ser-Ile-Pro-Ala (SEQ ID NO:1); and
   wherein the ADNF III polypeptide is selected from the group consisting of:
   Gly-Gly-Asn-Ala-Pro-Val-Ser-Ile-Pro-Gln (SEQ ID NO:20);
   Leu-Gly-Gly-Asn-Ala-Pro-Val-Ser-Ile-Pro-Gln-Gln-Ser (SEQ ID NO:21);
   Leu-Gly-Leu-Gly-Gly-Asn-Ala-Pro-Val-Ser-Ile-Pro-Gln-Gln-Ser (SEQ ID NO:22);
   Ser-Val-Arg-Leu-Gly-Leu-Gly-Gly-Asn-Ala-Pro-Val-Ser-Ile-Pro-Gln-Gln-Ser (SEQ ID NO:23); and
   Asn-Ala-Pro-Val-Ser-Ile-Pro-Gln (SEQ ID NO:2).

13. The method of claim 1, wherein the ADNF I polypeptide comprises up to about 20 amino acids at one or both of the N-terminus and the C-terminus of the active core site of the ADNF I polypeptide, and wherein the ADNF III polypeptide comprises up to about 20 amino acids at one or both of the N-terminus and the C-terminus of the active core site of the ADNF III polypeptide.

14. The method of claim 1, wherein the ADNF I polypeptide is a full length ADNF I polypeptide and the ADNF III polypeptide is a full length ADNF III polypeptide.

15. The method of claim 1, wherein the subject is afflicted with a neuropathology.

16. The method of claim 1, wherein the subject has Alzheimer's disease.

17. The method of claim 1, wherein the subject has Down's syndrome.

18. The method of claim 1, wherein the subject is normal.

19. The method of claim 18, wherein the subject is old.

20. The method of claim 1, wherein the method improves short term memory.

21. The method of claim 1, wherein the method improves reference memory.

22. The method of claim 1, wherein the mixture is administered intranasally or orally.

* * * * *

```
                            SEQUENCE LISTING

<160> NUMBER OF SEQ ID NOS: 23
<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I) active
      core site, SAL or ADNF-9

<400> SEQUENCE: 1

Ser Ala Leu Leu Arg Ser Ile Pro Ala
  1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:Activity
      Dependent Neurotrophic Factor III (ADNF III)
      active core site, NAP or ADNF III-8

<400> SEQUENCE: 2

Asn Ala Pro Val Ser Ile Pro Gln
  1               5

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence:Activity
      Dependent Neurotrophic Factor I (ADNF I)
      polypeptide formula
<220> FEATURE:
<221> NAME/KEY: MOD_RES
<222> LOCATION: (1)..(40)
<223> OTHER INFORMATION: Xaa = any amino acid, may be present or absent
<220> FEATURE:
<221> NAME/KEY: MOD_RES
<222> LOCATION: (50)..(89)
<223> OTHER INFORMATION: Xaa = any amino acid, may be present or absent

<400> SEQUENCE: 3

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
                 20                  25                  30

Xaa Xaa Xaa Xaa Xaa Xaa Xaa Xaa Ser Ala Leu Leu Arg Ser Ile Pro
         35                  40                  45

Ala Xaa Xaa Xaa Xaa Xaa Xaa Xaa Xaa Xaa Xaa Xaa Xaa Xaa Xaa Xaa
  50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa
                 85

<210> SEQ ID NO 4
<211> LENGTH: 5
```

```
<212> TYPE: PRT
<213> ORGANISM: Artificial Sequence
<220> FEATURE:
<223> OTHER INFORMATION: Description of Artificial Sequence:1-R and 2-R
      amino acid sequence from ADNF I polypeptide
      formula

<400> SEQUENCE: 4

Val Leu Gly Gly Gly
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:2-R amino
      acid sequence from ADNF I polypeptide formula

<400> SEQUENCE: 5

Val Leu Gly Gly
 1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence:2-R amino
      acid sequence from ADNF I polypeptide formula

<400> SEQUENCE: 6

Val Leu Gly Gly Val
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:2-R amino
      acid sequence from ADNF I polypeptide formula

<400> SEQUENCE: 7

Gly Val Leu Gly Gly
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence:3-R and 4-R
      amino acid sequence from ADNF III polypeptide
      formula

<400> SEQUENCE: 8

Leu Gly Leu Gly Gly
 1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:4-R amino
      acid sequence from ADNF III polypeptide formula

<400> SEQUENCE: 9
```

```
Leu Gly Leu Gly
 1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:4-R amino
      acid sequence from ADNF III polypeptide formula

<400> SEQUENCE: 10

Leu Gly Leu Gly Leu
 1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:preferred
      1-R amino acid sequence from ADNF I polypeptide formula

<400> SEQUENCE: 11

Val Glu Glu Gly Ile Val Leu Gly Gly Gly
 1               5                  10

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:preferred
      3-R amino acid sequence from ADNF III polypeptide formula

<400> SEQUENCE: 12

Ser Val Arg Leu Gly Leu Gly Gly
 1               5

<210> SEQ ID NO 13
<211> LENGTH: 88
<212> TYPE: PRT
<213> ORGANISM: Artificial Sequence
<220> FEATURE:
<223> OTHER INFORMATION: Description of Artificial Sequence:Activity
      Dependent Neurotrophic Factor III (ADNF III)
      polypeptide formula
<220> FEATURE:
<221> NAME/KEY: MOD_RES
<222> LOCATION: (1)..(40)
<223> OTHER INFORMATION: Xaa = any amino acid, may be present or absent
<220> FEATURE:
<221> NAME/KEY: MOD_RES
<222> LOCATION: (49)..(88)
<223> OTHER INFORMATION: Xaa = any amino acid, may be present or absent

<400> SEQUENCE: 13

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Asn Ala Pro Val Ser Ile Pro Gln
            35                  40                  45

Xaa Xaa Xaa Xaa Xaa Xaa Xaa Xaa Xaa Xaa Xaa Xaa Xaa Xaa Xaa
        50                  55                  60
```

```
Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa
                85
```

```
<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 14

Val Leu Gly Gly Gly Ser Ala Leu Leu Arg Ser Ile Pro Ala
 1               5                  10

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 15

Val Glu Glu Gly Ile Val Leu Gly Gly Gly Ser Ala Leu Leu Arg Ser
 1               5                  10                  15

Ile Pro Ala

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 16

Leu Gly Gly Gly Ser Ala Leu Leu Arg Ser Ile Pro Ala
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 17

Gly Gly Gly Ser Ala Leu Leu Arg Ser Ile Pro Ala
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 18

Gly Gly Ser Ala Leu Leu Arg Ser Ile Pro Ala
 1               5                  10
```

```
<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:ADNF I
      polypeptide

<400> SEQUENCE: 19

Gly Ser Ala Leu Leu Arg Ser Ile Pro Ala
  1               5                  10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 20

Gly Gly Asn Ala Pro Val Ser Ile Pro Gln
  1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 21

Leu Gly Gly Asn Ala Pro Val Ser Ile Pro Gln Gln Ser
  1               5                  10

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 22

Leu Gly Leu Gly Gly Asn Ala Pro Val Ser Ile Pro Gln Gln Ser
  1               5                  10                  15

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence:ADNF III
      polypeptide

<400> SEQUENCE: 23

Ser Val Arg Leu Gly Leu Gly Gly Asn Ala Pro Val Ser Ile Pro Gln
  1               5                  10                  15

Gln Ser
```